US006551599B2

(12) United States Patent
Mandrell et al.

(10) Patent No.: US 6,551,599 B2
(45) Date of Patent: Apr. 22, 2003

(54) MONOCLONAL ANTIBODIES AGAINST CAMPYLOBACTER JEJUNI AND CAMPYLOBACTER COLI OUTER MEMBRANE ANTIGENS

(75) Inventors: Robert E. Mandrell, Sonoma, CA (US); Anna H. Bates, Lafayette, CA (US); David L. Brandon, Berkeley, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/810,873

(22) Filed: Mar. 16, 2001

(65) Prior Publication Data

US 2002/0106383 A1 Aug. 8, 2002

Related U.S. Application Data

(62) Division of application No. 09/277,599, filed on Mar. 26, 1999.
(60) Provisional application No. 60/080,166, filed on Mar. 31, 1998.

(51) Int. Cl.[7] .............................................. A61K 39/02
(52) U.S. Cl. ................... 424/234.1; 424/130.1; 424/141.1; 424/150.1; 424/164.1; 530/387.1; 530/388.1; 530/388.2; 530/388.4; 530/387.5; 435/70.2; 435/70.21
(58) Field of Search ...................... 530/350, 387.1, 530/388.1, 388.2, 388.4, 387.5; 424/130.1, 141.1, 150.1, 164.1; 435/70.2, 70.21

(56) References Cited

U.S. PATENT DOCUMENTS 5,200,344 A 4/1993 Blaser et al.
5,470,958 A 11/1995 Blaser et al.

FOREIGN PATENT DOCUMENTS

WO WO 95/05850 3/1995

OTHER PUBLICATIONS

Willis, WL et al, Poultry Science, Feb 1997, vol. 76(2), pp. 314–317, abstract only.*
Blankenship, LC et al, Journal of Food Protection, vol. 46(6), pp. 510–513, 1983 abstract only.*
Moran, AP et al, Mar. 1989, pp. 253–260, vol. 97(3), APMIS, Serological analysis of heat stable antigens involved in serotyping Campylobacter jejuni and Campylobacter coli.*
Yuki, N et al, Journal of neurological sciences, May 1995, vol. 130(1), pp. 112–116.*
Bolla, JM et al, Conference:Campylobacter, Helicobacter and amp; Sep. 15–19, 1997, Cape Town, South Africa, pp. 280–283, International Workshop; 9th.*
Huyet, M et al, Abstracts of the Annual Meeting Am. Soc. Microbiology, vol. 87(0), Mar. 1–6, 1987, p. 234, abstract K190.*

(List continued on next page.)

Primary Examiner—Lynette R. F. Smith
Assistant Examiner—Ginny Allen Portner
(74) Attorney, Agent, or Firm—Margaret A. Connor; Thanda Wai; John Fado

(57) ABSTRACT

The present invention is directed to a method of producing monoclonal antibodies that are highly specific for (1) unique epitopes of Campylobacter jejuni (Cj) only and (2) epitopes conserved between Campylobacter jejuni and Campylobacter coli (Cc) outer membranes; to specific monoclonal antibodies made by the methods of the instant invention; and uses thereof The invention is drawn further to immunogens comprising the outer membrane complexes of Cj and Cc.

4 Claims, 26 Drawing Sheets

OTHER PUBLICATIONS

Mandrell, RE et al, abstract P50, p. 412, Abstracts of the Annual Meeting Am. Soc. Microbiologist, May 17–21, 1998.*

Moutinho–Fragoso et al, International Workshop of Campylobacter, Helicobacter and amp. 9th, Sep. 1997, pp. 312–316.*

Riverson, EA et al, 86th Annual Meeting of the American Society of Microbiology, vol. 86(0), pp. 422, 1986, Mar. 23–28, 1986 "A monoclonal antibody reactive against *Campylorbacter jejuni* and *Campylobacter coli*.", #V–16, abstract only.*

Wong, PCK et al, Abstracts of the General Meeting of the American Scoiety of Microbiology, vol. 95(0), May 21–25, 1995, abstract P–53, p. 391, abstract only.*

Yoshida, S et al, Am. J. Vet. Res., vol. 48(5), May 1987, pp. 801–804 (best copy possible).*

Yuki, N et al, Journal of neurological sciences, May 1995, vol. 130(1), pp. 112–116.*

Amako, K., et al., "Electron Microscopy of the Major Outer Membrane Protein of *Campylobacter jejuni*," *Microbiol. Immunol.* (1996) 40(10):749–754.

Bacon, D.J. *Dissertation Abstracts International* (Oct. 1997) 58(4):1665–B.

Bacon, D.J. et al., "Identification and Characterization of cytotoxic porin–lipopolysaccharide complex from *Campylobacter jejuni*," *J. Med. Microbiol.* (1999) 48:139–148.

Barroso, D. et al. *Microb Ecol. Health Dis.* (Oct. 1991) 4 (spec. issue):S25.

Bolla, J–M et al., "Conformational Analysis of the *Campylobacter jejuni* Porin," *Journal of Bacteriology* (1995) 177(15):4266–4271.

Brooks, B.W. et al., "Specificity of Monoclonal Antibodies to *Campylobacter jejuni* Lipopolysaccharide Antigens," *Immunological Investigations* (1998) 27(4&5):257–265.

Chalyaroj, S.C. et al., "Production of Monoclonal Antibody Specific to *Campylobacter jejuni* and Its Potential in Diagnosis of *Campylobacter Enteritis*," *Asian Pacific Journal of Allergy and Immunology* (1995) 13:55–61.

Chart, H. et al., "Outer Membrane Characteristics of *Campylobacter jejuni* grown in Chickens," FEMS *Microbiology Letters*, (Dec. 1996) 145:469–472.

Griffiths, P.L. et al., *J. of Applied Bacteriology* (1992) 72:467–474.

Guerry, P. "Nonlipopolysaccharide Surface Antigens of Campylobacter Species," J. *Infectious Diseases* (Dec. 1997) 176(suppl 2):S122–S124.

Harlow, E. et al., *Antibodies: A Laboratory Manual* (1998) 55–133.

Huyer, M. et al., "Outer Membrane Porin Protein of *Campylobacter jejuni*," *FEMS Microbiology Letters* (1986) 37(3):247–250.

Kosunen, T.U. et al., "Analysis of *Campylobacter jejuni* Antigens with Monoclonal Antibodies," Journal of Clinical Microbiology (1984) 19:129–133.

Kuan, S.K.C. et al., "Production of a Monoclonal Antibody that Recognizes the Lipopolysaccharide of a Campylobacter– Like Organism," *Microbiol. Immunol.* (1992) 36(8):791–801.

Lam, K.M., "Use of 45 kDa Protein in the Detection of *Campylobacter jejuni*," Avian *Pathology* (1992) 21(4):643–650.

Lamoureux, M. et al., "Detection of *Campylobacter jejuni* in Food and Poultry Viscera Using Immunomagnetic Separation and Microtitre Hybridization," *Journal of Applied Microbiology* (1997) 83:641–651.

Lu, P. et al., "Characterization of Monoclonal Antibodies for the Rapid Detection of Foodborne Campylobacter," *International Journal of Food Microbiology* (1997) 37:87–91.

Monfort, J.D. et al., "Detection of Flagellar Antigen of *Campylobacter jejuni* and *Campylobacter coli* in Canine Faeces with an Enzyme–Linked Immunosorbent Assay (ELISA) –New Prospects for Diagnosis," *Veterinary Research Communication* (1994)18(2):85–92.

Moser, I. et al., "In vitro binding og *Campylobacter jejuni/ coli* outer membrane preparations to INT 407 cell Membranes," *Med. Microbiol Immunol.* (1992) 180(6):289–303.

Nachamkin, I. et al., "Common and Specific Epitopes of *Campylobacter Flagellin* Recognized by Monoclonal Antibodies," *Infection Immunity* (Aug. 1986) 52(2):438–440.

Page, W.J. et al., "Comparison of Methods Using to Separate the Inner and Outer Membranes of Cell Envelopes of *Campylobacter spp.*," *Journal of General Microbiology* (Nov. 1988) 134(pt11):2925–2932.

Page, W.J. et al., "Characterization of the Porins of *Campylobacter jejuni* and *Campylobacter coli* and Implications for Antibiotic Susceptibility," *Antimicrobial Agents and Chemotherapy* (Mar. 1989) 33:(3):297–303.

Rice, B.E. et al., "Development of a Rapid and Specific Colony–Lift Immunoassay for Detection and Enumeration of *Campylobacter jejuni, . Coli*, and *C. Lari,*" *Clinical and Diagnostic Laboratory Immunology* (1996) 3(6):669–677.

Schroder, W. et al., "Primary Structure Analysis and Adhesion Studies on the Major Outer Membrane Protein of *Campylobacter jejuni,*" *FEMS Microbiology Letters* (May 1997) 150(10):141–147.

Stills Jr., H.F. et al., "Utilization of Monoclonal Antibodies to Evaluate the Involvement of *Campylobacter jejuni* in Proliferative Ileitis in Syrian Hamsters (*Mesocricetis auratus*)," *Infection Immunity* (Sep. 1987) 55(9):2240–2246.

Wirguin, I. et al., "Monoclonal IgM Antibodies to GM1 and Asialo–GM1 in Chronic Neuropathies Cross–React with *Campylobacter jejuni* Lipopolysaccharides," *American Neurological Association* (Jun. 1994) 35(6):698–703.

Yuki, N. et al., "Penner's Serotype 4 of *Campylobacter jejuni* Has a Lipopolysaccharide That Bears a GM1 Ganglioside Epitope as well as One That Bears a GD1a Epitope," *Infection and Immunity* (May 1994) 62(5):2101–2103.

Zhang, J. et al., "The *Campylobacter jejuni* Porin Timers Pack into Different Lattice Types When Reconstituted in the Presence of Lipid," *Eur. J. Biochem.* (1997) 244:575–579.

* cited by examiner

+=0.3 TO 0.5;  ++=0.5 TO 0.8;  +++=0.8 TO 1.2;  ++++= >1.2

| Fusion Plate | COL-UMN | ROW | Clone# | Cj O:1 | Cj O:2 | Cj O:3 | Cj O:4 | Cj O:19 | Cj O:23 | Cc O:30 | Cj O:36 | Cj RM1221 | Cj RM1222 |
|---|---|---|---|---|---|---|---|---|---|---|---|---|---|
| 1 | A | 1 | Uncloned | | | | | | | | | | |
| 1 | A | 3 | C752 | + | | | | | | | | | |
| 1 | A | 6 | C755 | | | | | | | | | ++ | ++ |
| 1 | A | 8 | C756 | | | | | | | | | +++ | +++ |
| 1 | A | 9 | C757 | | | | | | | | | + | + |
| 1 | B | 2 | C752 | +/- | + | | | | | | | | |
| 1 | B | 2 | C755 | + | ++ | ++ | +++ | + | ++ | | +/- | +++ | +++ |
| 1 | B | 2 | C756 | + | ++ | +++ | +++ | + | ++ | | + | +++ | ++++ |
| 1 | B | 2 | C757 | + | ++ | +++ | +++ | + | ++ | | + | +++ | +++ |
| 1 | B | 2 | C782 | | ++ | +++ | ++++ | ++ | +++ | | + | ++++ | +++ |
| 1 | B | 2 | C793 | | + | | | | | | | | |
| 1 | B | 2 | C794 | +++ | ++++ | +++ | +++ | ++ | ++ | ++ | ++ | +++ | ++ |
| 1 | B | 7 | DISCARD | | | | | | | | | | |
| 1 | C | 5 | C722 | - | - | - | - | - | - | - | - | - | - |
| 1 | C | 5 | C723 | - | - | - | - | - | - | - | - | - | - |
| 1 | C | 5 | C764 | - | - | - | - | - | - | - | - | - | - |

Figure 10A

| Fusion Plate | COL-UMN | ROW | Clone# | CjO:1 | CjO:2 | CjO:3 | CjO:4 | CjO:19 | CjO:23 | CcO:30 | CjO:36 | Cj RM1221 | Cj RM1222 |
|---|---|---|---|---|---|---|---|---|---|---|---|---|---|
| 1 | D | 3 | C744 | ++ | +++ | +++ | +++ | +++ | ++ | ++ | ++ | ++++ | ++++ |
| 1 | E | 3 | | +++ | ++++ | +++ | ++++ | +++ | +++ | ++++ | ++ | ++++ | ++++ |
| 1 | E | 12 | DISCARD | | | | + | | | | | | + |
| 1 | F | 7 | C742 | ++ | +++ | ++ | +++ | ++ | ++ | ++++ | ++ | +++ | ++++ |
| 1 | G | 4 | | | + | + | | | | | | + | + |
| 1 | H | 9 | DISCARD | | ++ | + | + | | | | | | ++ |
| 1 | A | 4 | | ++++ | ++++ | ++++ | ++++ | ++++ | | | ++ | ++++ | +++ |
| 2 | A | 6 | DISCARD | ++ | + | ++ | ++ | +++ | + | | ++ | ++ | + |
| 2 | A | 12 | | | | | +++ | + | | | | | |
| 2 | B | 1 | DISCARD | +++ | ++ | +++ | ++++ | +++ | ++ | + | +++ | ++++ | ++ |
| 2 | B | 4 | | | | | | + | ++ | + | | | |
| 2 | C | 8 | | | + | ++ | | | | | | | |
| 2 | C | 11 | DISCARD | | | +++ | ++ | +++ | | | | ++++ | ++++ |
| 2 | C | 12 | C701,C702 | | | ++ | | | + | + | + | ++ | ++ |
| 2 | E | 1 | | | | + | ++ | + | | | | + | ++ |
| 2 | F | 12 | | + | + | + | ++ | | + | | + | | |

Legend: += 0.3 TO 0.5;  ++=0.5 TO 0.8;  +++=0.8 TO 1.2;  ++++= >1.2

| Fusion Plate | COLUMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 2 | G | 4 |  | +++ | ++++ | ++++ | ++++ | ++++ | ++++ | +++ | ++++ | ++++ | ++++ |
| 2 | G | 5 |  | ++ | ++ | ++ | ++ | ++ |  |  | + | ++ | +++ |
| 2 | G | 11 | DISCARD |  | + |  |  |  |  |  |  |  | +++ |
| 2 | G | 12 |  |  |  | + | + | + |  |  |  | + | + |
| 2 | H | 4 |  |  | + | +++ | +++ | ++ |  | + |  | + | ++ |
| 2 | H | 5 |  |  | + | ++ | ++ | + | + |  |  | + | + |
| 3 | A | 10 |  |  |  | + | ++ |  |  |  |  |  | + |
| 3 | A | 12 | DISCARD |  |  |  |  |  |  |  |  |  | + |
| 3 | B | 3 |  |  | + |  | + |  | + |  |  | + | ++ |
| 3 | C | 7 |  |  | + |  |  |  |  |  |  | + | ++ |
| 3 | C | 10 |  | ++ |  | + | +++ |  |  |  |  |  | ++ |
| 3 | D | 2 | C714, C715 | + | ++ | ++ | +++ |  | ++ |  |  | ++ | +++ |
| 3 | E | 8 |  |  |  |  |  | ++++ |  |  |  |  |  |
| 4 | B | 8 |  |  | + | ++ | ++ |  |  |  |  | ++ |  |
| 4 | B | 10 |  | ++ | +++ | +++ | +++ |  | +++ | +++ | ++ | ++++ | ++++ |
| 4 | B | 11 |  |  | + | + | + |  |  |  |  | + | + |
| 4 | C | 9 |  |  |  |  |  |  |  |  | + | + | + |
| 4 | D | 5 |  | + | ++ | ++ | + |  | + |  | + | ++ | ++ |

Legend: += 0.3 TO 0.5;  ++= 0.5 TO 0.8;  +++= 0.8 TO 1.2;  ++++ = >1.2

| Fusion Plate | COLUMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 4 | E | 6 | | | | | | | | | | + | + |
| 4 | F | 4 | | | | | | | | | | ++ | ++ |
| 4 | G | 1 | | | | | | ++ | | | | + | + |
| 5,6,7 | A | 2 | | ++ | | + | + | | | | | +++ | + |
| 5,6,7 | A | 3 | | | ++++ | ++++ | ++++ | ++++ | +++ | | +++ | ++++ | ++++ |
| 5,6,7 | A | 4 | | | + | | + | | | | | + | +++ |
| 5,6,7 | B | 1 | | | | + | | | | | | | |
| 5,6,7 | B | 4 | | | | | + | | + | | | | |
| 5,6,7 | B | 5 | DISCARD | | | | | | | | | | |
| 5,6,7 | C | 1 | | | + | ++ | +++ | + | + | | + | | |
| 5,6,7 | C | 2 | | +++ | ++++ | ++ | ++++ | ++ | +++ | ++++ | ++++ | +++ | +++ |
| 5,6,7 | C | 3 | | | +++ | ++ | ++++ | +++ | +++ | ++++ | +++ | ++++ | ++++ |
| 5,6,7 | C | 4 | | | + | + | + | | | | | | |
| 5,6,7 | D | 1 | | | | + | ++ | | + | | + | ++ | + |
| 5,6,7 | D | 4 | | | | | | | | | | | |
| 5,6,7 | F | 4 | | | | + | ++ | + | | ++ | | ++ | ++ |
| 5,6,7 | G | 1 | | | | | | | | ++ | | | |

| Fusion Plate | COL-UMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 1 | A | 1 |  |  |  |  |  |  |  |  |  |  |  |
| 1 | A | 3 |  |  | ++ | ++ |  | ++ | + |  |  | ++ | ++ |
| 1 | B | 12 |  |  | + |  |  |  |  |  | ++ | + | + |
| 1 | C | 1 |  |  |  | + |  |  |  |  |  |  |  |
| 1 | C | 3 |  | + | +++ | + | ++ | ++ | + |  |  |  |  |
| 1 | C | 5 |  | +++ | ++++ | +++ | +++ | +++ |  |  |  |  |  |
| 1 | C | 6 |  | ++ | +++ | ++ |  |  |  |  |  | +++ | ++ |
| 1 | D | 1 |  |  |  |  |  |  |  |  |  | +++ | +++ |
| 1 | D | 7 |  |  | +++ | +++ | +++ | + | + |  | ++ | ++++ | ++++ |
| 1 | E | 3 |  |  | ++ | ++ | ++ | ++ |  | ++ |  | ++++ | ++++ |
| 1 | E | 7 |  |  |  |  |  |  | +++ |  | + | +++ | ++ |
| 1 | E | 9 |  |  | + |  | + |  | ++ |  |  | ++ | + |
| 1 | E | 10 |  |  | +++ | + | ++ |  |  |  |  | +++ | + |
| 1 | F | 4 |  |  |  |  |  |  |  |  | + | ++ | ++ |
| 1 | F | 5 |  |  | +++ | + | +++ | + |  |  | + | +++ | +++ |
| 1 | F | 8 |  |  |  |  |  |  |  |  |  |  |  |
| 1 | F | 10 |  |  |  |  |  |  |  |  |  | + |  |
| 1 | G | 6 |  | + |  |  |  |  |  |  |  |  |  |
| 1 | H | 10 |  |  |  |  |  | + | ++ |  |  | ++ | ++ |

Figure 11B

Legend: += 0.3 TO 0.5;  ++= 0.5 TO 0.8;  +++= 0.8 TO 1.2;  ++++ = >1.2

| Fusion Plate | COLUMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 2 | A | 4 |  | ++ |  |  |  |  |  |  |  |  |  |
| 2 | A | 5 |  | +++ | ++++ | +++ | ++++ | +++ | ++++ |  | ++++ | ++++ | ++++ |
| 2 | A | 8 |  | +++ |  |  |  |  |  |  |  |  |  |
| 2 | A | 12 |  | + |  | + | + |  |  |  |  | ++ | ++ |
| 2 | B | 2 |  | + | ++ | ++ | + |  |  |  |  |  | + |
| 2 | B | 5 |  | + |  |  |  | ++++ | ++ |  | +++ | + | +++ |
| 2 | B | 8 |  |  | ++ | ++ |  | + | + | +++ | + | + | + |
| 2 | B | 10 |  | ++ | +++ | ++ | ++ |  |  | + |  |  |  |
| 2 | B | 11 |  | + | ++ | ++ | +++ | + |  |  |  | + |  |
| 2 | C | 4 |  | ++ | ++ |  | + | + | + |  | + |  |  |
| 2 | C | 6 |  | + |  |  |  |  |  |  |  |  |  |
| 2 | C | 9 |  |  |  |  |  |  |  |  |  | +++ | +++ |
| 2 | D | 6 |  | ++ | +++ | ++ | ++ | + | ++ |  |  | +++ | ++ |
| 2 | E | 6 |  | + |  | + | + |  |  |  |  | + | ++ |
| 2 | E | 8 |  | ++ | ++ |  | +++ | + |  |  |  | +++ | +++ |
| 2 | F | 3 |  |  | + | + |  |  |  |  |  | + | + |
| 2 | F | 4 |  |  |  |  | ++ |  |  |  |  | ++ | ++ |
| 2 | F | 9 |  |  |  |  |  |  |  |  |  |  |  |
| 2 | G | 5 |  | ++ |  |  |  |  |  |  |  |  |  |

| Fusion Plate | COL-UMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| | | | | +=0.3 TO 0.5; | ++=0.5 TO 0.8; | +++=0.8 TO 1.2; | ++++= >1.2 | | | | | | |
| 2 | G | 7 | | ++ | +++ | | | | | | | | +++ |
| 2 | G | 12 | | | +++ | ++ | ++ | | | | | +++ | +++ |
| 2 | H | 10 | | ++ | +++ | | | | | | | +++ | +++ |
| 3 | A | 1 | | | ++ | | ++ | | | | | | ++ |
| 3 | A | 2 | | | | | | | + | | | | + |
| 3 | A | 9 | | | | ++ | | ++ | | | | + | |
| 3 | A | 12 | | | | +++ | + | | | + | | | + |
| 3 | B | 6 | | | | + | | | | | | | |
| 3 | C | 1 | | ++ | | | | ++++ | | | | +++ | +++ |
| 3 | D | 11 | | + | + | ++ | | ++ | | | | ++ | ++ |
| 3 | E | 4 | | | +++ | ++ | + | + | + | | | +++ | ++ |
| 3 | E | 9 | | + | ++ | ++ | ++ | ++ | ++ | | | +++ | +++ |
| 3 | E | 12 | | | | | +++ | | + | | | +++ | |
| 3 | F | 10 | | + | + | + | +++ | +++ | | | | ++ | +++ |
| 3 | G | 7 | | | | | | | | | | ++ | +++ |
| 3 | H | 10 | | | | | | | | ++ | ++ | ++++ | +++ |
| 4 | A | 6 | | | | | | | | | +++ | ++ | ++ |
| 4 | A | 8 | | | | | | | | | | | |
| 4 | B | 4 | | | | | | | | | + | + | |

| Fusion Plate | COL-UMN | ROW | Clone# | Cj O:1 | Cj O:2 | Cj O:3 | Cj O:4 | Cj O:19 | Cj O:23 | Cc O:30 | Cj O:36 | Cj RM1221 | Cj RM1222 |
|---|---|---|---|---|---|---|---|---|---|---|---|---|---|
| 4 | B | 12 | | | | | | | | | | | + |
| 4 | C | 10 | | | | | | | | | | ++ | |
| 4 | D | 2 | | + | | | ++ | | | | ++ | ++ | ++ |
| 4 | D | 6 | | | ++ | | | | | | | | |
| 4 | D | 7 | | | | | + | | | + | | | |
| 4 | E | 1 | | + | ++ | ++ | +++ | += | | | ++ | +++ | +++ |
| 4 | E | 10 | | +++ | +++ | +++ | ++++ | ++ | | ++ | +++ | ++++ | ++++ |
| 4 | G | 2 | | ++ | ++ | + | +++ | +++ | | +++ | +++ | +++ | +++ |
| 4 | G | 8 | | + | + | ++++ | +++ | +++ | | + | ++ | +++ | +++ |
| 4 | H | 6 | | | + | +++ | + | | | | + | +++ | +++ |
| 5 | A | 3 | | | + | + | + | | + | | | | |
| 5 | A | 4 | | | + | | ++ | ++ | ++ | | | + | + |
| 5 | A | 6 | | | | | | | | | | | |
| 5 | A | 11 | | ++++ | ++ | +++ | | ++++ | + | | | ++++ | +++ |
| 5 | B | 4 | | | ++ | ++++ | | | ++ | | | +++ | +++ |
| 5 | B | 11 | | | ++ | + | ++ | | + | | | ++ | ++ |
| 5 | C | 3 | | | | +++ | | ++ | | | + | | |
| 5 | C | 9 | | | | | | ++ | | | | | |
| 5 | C | 12 | | | + | + | +++ | + | + | | | ++ | ++ |

| Fusion Plate | COLUMN | ROW | Clone# | Cj O:1 | Cj O:2 | Cj O:3 | Cj O:4 | Cj O:19 | Cj O:23 | Cc O:30 | Cj O:36 | Cj RM1221 | Cj RM1222 |
|---|---|---|---|---|---|---|---|---|---|---|---|---|---|
| 5 | D | 3 | | + | + | | | | | | | ++ | ++ |
| 5 | D | 10 | | ++ | +++ | ++ | +++ | | | | | +++ | ++++ |
| 5 | D | 11 | | | +++ | + | ++ | | | | | ++ | +++ |
| 5 | E | 4 | | + | +++ | ++ | +++ | | + | | | +++ | ++++ |
| 5 | E | 11 | | ++++ | ++++ | +++ | ++++ | ++++ | ++++ | + | ++ | ++++ | ++++ |
| 5 | F | 9 | | | ++ | ++ | ++ | + | +++ | | | ++ | +++ |
| 5 | F | 11 | | ++++ | +++ | ++++ | ++ | + | ++++ | | | ++++ | ++++ |
| 5 | G | 6 | | | | ++ | ++ | ++++ | ++ | | | ++ | ++ |
| 5 | G | 7 | | | | | | ++++ | | | | ++ | |
| 5 | G | 10 | | | | + | | | ++ | | +++ | | +++ |
| 5 | G | 12 | | | + | + | | | | | | | |
| 5 | H | 4 | | | + | | ++ | | | | | | ++++ |
| 5 | H | 5 | | + | + | + | | | | | | | |
| 6 | A | 3 | | +++ | + | + | + | | | | + | +++ | +++ |
| 6 | A | 4 | | ++ | + | ++ | +++ | | | ++ | ++ | + | ++++ |
| 6 | B | 1 | | ++++ | + | + | ++ | | | ++ | +++ | ++ | +++ |
| 6 | B | 2 | | ++ | | | + | | | ++ | ++ | ++++ | + |
| 6 | B | 4 | | | | | | | | +++ | | +++ | +++ |
| 6 | B | 5 | | | + | | | | ++++ | ++++ | ++++ | | ++ |

Legend: += 0.3 TO 0.5;  ++= 0.5 TO 0.8;  +++= 0.8 TO 1.2;  ++++= >1.2

| Fusion Plate | COLUMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 6 | B | 6 |  | +++ | ++ |  |  |  |  |  |  |  | ++ |
| 6 | B | 7 |  | ++++ | ++++ | ++ | ++++ | +++ |  | ++ | +++ | ++++ | +++ |
| 6 | B | 9 |  | ++++ | + | +++ | +++ |  |  | ++++ | ++++ | +++ | + |
| 6 | B | 12 | #REF! | ++++ | ++++ | ++++ | ++++ | ++++ |  | +++ | ++++ | ++++ | ++++ |
| 6 | C | 7 |  | + | + | + | + |  |  | + | ++ | ++ | ++ |
| 6 | C | 5 |  | +++ | ++++ | +++ | ++ | +++ | ++ | ++ | +++ | +++ | +++ |
| 6 | D | 5 |  | +++ | +++ | +++ | ++ | ++ | + | ++ | ++ | +++ | +++ |
| 6 | D | 7 |  | ++ | ++ | ++ | ++ | + | ++ | + | ++ | ++ | ++ |
| 6 | E | 1 |  | + | + | + | + |  | + | ++ | ++ | + | ++ |
| 6 | E | 5 |  | + | ++ |  | ++ | + |  | + | ++ | + | ++ |
| 6 | E | 7 |  | ++++ | +++ | ++++ | ++++ | ++ |  | + | ++ | ++++ | ++++ |
| 6 | E | 9 |  | ++ | + | + | + |  |  |  | + | + | + |
| 6 | F | 1 |  | + | + |  |  |  |  |  |  |  | ++ |
| 6 | F | 3 |  |  | ++ |  |  |  |  |  |  |  |  |
| 6 | F | 5 |  | + | +++ |  |  |  |  | ++ |  | ++++ | ++ |
| 6 | F | 6 |  | + | + |  |  |  |  |  | + | + | ++ |
| 6 | F | 9 |  |  |  |  |  | + |  |  |  |  |  |
| 6 | F | 10 |  | ++++ | +++ | ++ | ++ | + | + | + | + | ++ | +++ |
| 6 | G | 2 |  | ++++ | ++++ |  |  |  |  |  |  |  | ++ |

| Fusion Plate | COLUMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 6 | G | 11 |  |  |  |  |  |  |  |  |  |  |  |
| 7 | A | 5 |  |  |  |  |  |  |  |  |  | + | ++++ |
| 7 | A | 9 |  |  |  |  |  |  |  |  |  | + | ++ |
| 7 | A | 11 |  |  |  |  |  |  |  |  |  | + | + |
| 7 | B | 1 | ++++ | ++++ |  | +++ | +++ | ++ |  | + | + | +++ |
| 7 | B | 2 | ++ | ++ |  |  | +++ | + |  |  | + | ++ |
| 7 | B | 7 | +++ | ++ | +++ | ++ | +++ | +++ |  | +++ | ++ | ++++ |
| 7 | B | 8 |  | ++ | ++ | ++++ |  | ++ |  |  | ++++ | ++++ |
| 7 | C | 2 | ++ | ++++ | +++ | +++ | ++ | +++ | ++ |  | ++ | +++ |
| 7 | C | 3 | ++ | +++ | ++ | ++ | +++ | ++ | ++ |  | +++ | ++++ |
| 7 | C | 4 | ++++ | ++++ | ++++ | +++ | +++++ | ++++ | ++++ | +++ | ++++ | ++++ |
| 7 | C | 5 | ++ | +++ | ++++ | ++ | ++ | ++ |  |  | ++ | +++ |
| 7 | C | 6 | ++++ | ++++ | ++++ | ++ | +++++ | ++++ |  | +++ | ++++ | ++++ |
| 7 | C | 7 | ++++ | ++++ | ++++ | +++ | ++++ | ++++ |  |  | ++++ | ++++ |
| 7 | C | 9 |  | ++ |  | +++ | ++ | ++ |  |  | ++ | ++ |
| 7 | C | 10 | +++ | ++++ |  | +++ | + | ++ |  |  | + | ++ |
| 7 | D | 1 | ++++ | ++++ | + |  |  |  |  |  | ++ | ++ |
| 7 | D | 8 | +++ |  | ++++ | ++++ | ++++ | ++++ |  |  | ++++ | ++++ |

| Fusion Plate | COL-UMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 7 | D | 9 |  | ++ | +++ | ++++ | ++ | ++++ | ++++ |  |  | +++ | ++++ |
| 7 | D | 12 |  |  |  |  | ++ |  | ++ |  |  | ++ | +++ |
| 7 | E | #REF! |  | + | ++ | ++ | + | ++++ | ++++ |  |  | ++++ | ++++ |
| 7 | E | 2 |  | ++ | +++ | +++ | ++++ | ++++ |  | ++++ | ++ | +++ | +++ |
| 7 | E | 3 |  | ++++ | +++ | +++ | ++++ | ++++ | ++ |  |  | +++ | ++++ |
| 7 | E | 4 |  | ++ | +++ | ++ | + | ++++ | ++ |  |  | + | +++ |
| 7 | E | 6 |  |  | ++ |  |  | ++ | +++ |  |  | +++ | +++ |
| 7 | E | 7 |  |  | ++ | ++ |  | ++ |  |  | ++ | ++ | +++ |
| 7 | E | #REF! |  |  | + |  |  |  | ++ |  |  |  | ++ |
| 7 | E | 9 |  | +++ | ++ | ++ | ++++ | ++++ | ++ |  |  | +++ | +++ |
| 7 | E | 10 |  | + |  |  | +++ | ++++ | ++++ | ++++ | +++ | ++++ | ++++ |
| 7 | F | 2 |  |  |  |  | + | ++++ | +++ | ++ | + | ++ | +++ |
| 7 | F | 3 |  |  |  |  |  |  |  |  |  |  |  |
| 7 | F | 5 |  |  |  |  |  |  |  |  |  |  |  |
| 7 | F | 6 |  |  |  |  |  |  |  |  |  |  |  |
| 7 | F | 7 |  |  |  |  |  |  |  |  |  |  |  |
| 7 | F | #REF! |  | +++ | ++ | ++ | +++ | ++++ | ++++ |  | +++ | ++++ | ++++ |
| 7 | F | 11 |  |  |  |  |  | ++++ | +++ |  |  | +++ | ++++ |
| 7 | G | 1 |  |  | +++ |  | ++ | ++++ | ++++ |  | + | +++ | +++ |

+=0.3 TO 0.5;  ++=0.5 TO 0.8;  +++=0.8 TO 1.2;  ++++= >1.2

| Fusion Plate | COL-UMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 7 | G | 5 |  |  |  | ++++ |  |  |  |  |  |  |  |
| 7 | G | 7 |  |  | ++ |  |  |  |  |  |  | + | ++ |
| 7 | G | 8 |  | +++ | +++ |  |  |  |  |  |  |  |  |
| 7 | G | 12 |  |  | ++ | ++ | ++ | ++ | ++ |  |  |  |  |
| 7 | H | 4 |  | ++ | + | ++++ | ++ | ++ | ++++ |  |  | ++ | ++++ |
| 7 | H | 6 |  | +++ | ++++ | ++++ | ++++ | ++++ | ++++ |  | +++ | ++++ | ++++ |
| 7 | H | 8 |  |  | ++ | ++ | +++ | ++ | ++ |  |  | ++ | ++ |
| 7 | H | 9 |  | +++ | +++ | ++++ | ++++ | ++ | ++++ |  |  | +++ | +++ |
| 7 | H | 12 |  |  | ++ |  | ++ |  | + |  |  | + | + |
| 8 | A | 9 |  |  | ++++ | +++ | ++++ |  |  | ++ |  | +++ | +++ |
| 8 | A | 12 |  |  | ++ | ++ | ++ |  |  |  |  | + | ++ |
| 8 | B | 1 |  |  | +++ | ++ | +++ |  |  |  |  | ++ | +++ |
| 8 | B | 2 |  |  | ++++ |  | ++ |  |  | ++ |  | +++ | ++++ |
| 8 | B | 4 |  |  | +++ |  |  |  |  |  |  | +++ | ++ |
| 8 | B | 7 |  | + |  |  | ++ |  |  |  |  | +++ | + |
| 8 | B | 8 |  | + |  | ++ |  | ++ | ++ | ++ | ++ | +++ | +++ |
| 8 | B | 10 |  |  | +++ |  |  |  |  |  |  | +++ | +++ |
| 8 | C | 6 |  |  | +++ |  |  |  |  |  |  | +++ | +++ |
| 8 | C | 7 |  |  | + |  | ++ |  |  |  |  | ++ | ++ |

| Fusion Plate | COLUMN | ROW | Clone# | Cj O:1 | Cj O:2 | Cj O:3 | Cj O:4 | Cj O:19 | Cj O:23 | Cc O:30 | Cj O36 | Cj RM1221 | Cj RM1222 |
|---|---|---|---|---|---|---|---|---|---|---|---|---|---|
| 8 | C | | #REF! | | | | | ++++ | | | | | |
| 8 | D | 1 | | + | ++++ | | ++ | | | | | +++ | +++ |
| 8 | D | 7 | | ++ | +++ | ++ | +++ | ++ | | | | ++++ | ++ |
| 8 | D | 11 | | + | ++++ | ++ | | | | | | +++ | ++++ |
| 8 | E | 3 | | | ++ | | | ++++ | | | | | |
| 8 | E | 4 | | | | | | +++ | | | | | |
| 8 | E | 6 | | ++++ | ++++ | +++ | +++++ | +++ | +++ | + | +++ | ++++ | ++++ |
| 8 | E | 8 | | + | +++ | ++ | | | ++ | | | ++ | ++ |
| 8 | E | 10 | | + | +++ | | +++ | ++ | +++ | | ++ | +++ | ++++ |
| 8 | E | 11 | | | | | | | ++ | | | ]+++ | +++ |
| 8 | E | 12 | | + | +++ | ++ | ++++ | ++ | ++ | | | + | + |
| 8 | F | 1 | | | | | | | | | ++ | +++ | +++ |
| 8 | F | 3 | | | ++ | | | | | | | ++ | ++ |
| 8 | F | 10 | | | | | ++ | | | | | + | ++ |
| 8 | G | 1 | | +++ | ++++ | +++ | +++ | ++ | ++++ | +++ | + | +++ | +++ |
| 8 | G | 2 | | +++ | +++ | +++ | +++ | ++ | ++++ | ++ | | ++++ | ++++ |
| 8 | G | 6 | | | | | | | | | | | ++ |
| 8 | H | 2 | | | | | | | | | | | |
| 8 | H | 6 | | ++ | +++ | +++ | +++ | ++ | ++++ | ++ | ++ | ++++ | ++++ |

| Fusion Plate | COLUMN | ROW | Clone# | Cj O:1 | Cj O:2 | Cj O:3 | Cj O:4 | Cj O:19 | Cj O:23 | Cc O:30 | Cj O:36 | Cj RM1221 | Cj RM1222 |
|---|---|---|---|---|---|---|---|---|---|---|---|---|---|
| 8 | H | 7  |  |   | +   | ++   |  |  |  |  |  | +++ | ++ |
| 8 | H | 10 |  | + | +++ | ++++ |  |  |  |  |  | +++ | ++++ |
| 8 | H | 11 |  | + | +++ | ++++ |  |  |  |  |  | ++  | ++++ |

Figure 11K

MONOCLONAL ANTIBODIES AGAINST *CAMPYLOBACTER JEJUNI* AND *CAMPYLOBACTER COLI* OUTER MEMBRANE ANTIGENS

CROSS-REFERENCE TO RELATED APPLICATIONS

This application is a divisional of pending application Ser. No. 09/277,599 filed Mar. 26, 1999, which is a non-provisional of provisional application Serial No. 60/080,166, filed Mar. 31, 1998 The prior applications are hereby incorporated herein by reference.

FIELD OF THE INVENTION

The present invention relates generally to a method of preparing an immunogen comprising outer membranes from *Campylobacter jejuni* (hereafter designated Cj) and *Campylobacter coli* (hereafter designated Cc), inoculating animals with the immunogen, and detecting the desired hybridoma-producing antibodies; and to a composition comprising the immunogen. The invention is drawn further to hybridoma cell lines developed by this method to produce (1) monoclonal antibodies specific to Cj only and (2) monoclonal antibodies that recognize both Cj and Cc exclusively, and uses thereof.

BACKGROUND OF THE INVENTION

Campylobacters cause more human gastroenteritis than any other food-borne pathogen. Campylobacter enteritis is caused by two closely related species, Cj and Cc, but Cj is responsible for greater than 98% of human disease and produces more severe symptoms. Cj, has been further subdivided into Cj subspecies *jejuni* (Cjj) and Cj subspecies *doylei* (Cjd). (In the remainder of this application, the term Cjj will be used to designate *C. jejuni* subspecies *jejuni* and Cjd to designate *C. jejuni* subspecies *doylei*. The term Cj (*Campylobacter jejuni*) will be used to describe both *C. jejuni* subspecies *jejuni* and *C. jejuni* subspecies *doylei* collectively.) Cjj and Cjd are closely related; however, Cjj is the predominant subspecies causing human illness and isolated from food sources. Cj and Cc cause acute diarrhea in humans with associated enteritis, particularly in developing countries. These infections are prevalent in infants under 1 year in age and rank as the third most common cause of acute diarrhea after Rotavirus and enterotoxigenic *Escherichia coli*. The various clinical patterns of disease suggest that Campylobacter spp. and, more specifically, Cj strains are diverse and may possess more than one type of virulence factor. In addition, Cj, unlike Cc, are more often associated with symptomatic infections and with bloody diarrhea.

Since Campylobacter enteritis is a considerable world health problem contributing to morbidity in developed countries and to high mortality rates in children in developing countries, it is of clinical importance to develop a specific and rapid diagnostic assay to identify pathogenic Campylobacter in the stool of enteritis patients. The available culture methods for detecting the organism generally are extremely time consuming and costly. Several studies have reported production of anti-Campylobacter MAbs and their use in immunoassays to detect Campylobacter infection (Chaiyaroj et al., 1995).

Campylobacter was not recognized as a human pathogen until the mid 1970's. Previously, the principal food-borne pathogen of concern had been Salmonella spp. Since the 1970s, the food industry and the regulatory agencies have become aware of the importance of other food-borne pathogens, such as *Yersinia enterocolitica, Escherichia coli* O157:H7, and *Listeria monocytogenes*. Very recently, Cj has become recognized as the most frequent cause of gastroenteritis in the U.S. and has been observed as the most common pathogen associated with Guillain-Barre syndrome in humans. It is estimated that about 1 in 1,000 Campylobacter infections results in this serious illness (Nachamkin et al., 1992).

Campylobacter is very prevalent in poultry (Madden et al., 1998) and contaminates milk (Docherty et al., 1996). Hazard analysis critical control point (HACCP) systems for poultry are being implemented internationally (Notermans et al., 1994), and beginning in 1997 in the U.S., large poultry processors have been required to meet performance standards for the frequency and amount of Salmonella in their product (Anonymous, 1996). It is anticipated that similar performance standards will be established for Campylobacter spp. as better culture and quantitative detection methods are developed. The development of rapid, reliable, and cost-effective methods for the detection of food-borne pathogens is crucial to accurately assess the safety of a food product, the effectiveness of new control measures to minimize pathogens in a production or processing environment, and the basic biology and ecology of pathogens in the food environment.

Campylobacters are known to be widespread in the environment and contaminate soil and water (Stanley et al., 1998). Environmental monitoring requires detection methods that are field-based, portable, rapid, and capable of analyzing multiple samples. Biosensors that contain specific immobilized antibodies to capture a pathogen for subsequent detection by a laser light or other sensitive detection system are being developed (Zhou et al., 1998). The specificity, sensitivity, and affinity of the antibody in a biosensor are key factors for success. The following U.S. patents are incorporated by reference.

U.S. Pat. No. 4,404,194 discloses a 90 kDa protein from *C. jejuni* that has immuno-suppressive activity.

U.S. Pat. No. 4,785,086 discloses a DNA probe for detecting *C. jejuni*.

U.S. Pat. No. 4,882,271, discloses a 300–700 kDa antigen from *Campylobacter pylori* and its use in various assays.

U.S. Pat. No. 4,942,126 discloses a method of identifying the presence of Campylobacter spp. in fecal specimens.

U.S. Pat. No. 5,200,344 discloses a method of identifying the presence of antibodies to *C. jejuni* or *C. coli* in test samples.

U.S. Pat. No. 5,374,531 discloses a method of analyzing particulate analytes, such as whole cells, in immunoassays.

U.S. Pat. No. 5,470,958 discloses an antigenic composition and antisera raised against a purified PEB 1 antigen from *C. jejuni*.

U.S. Pat. Nos. 5,491,068 and 5,695,946 disclose a method of capturing specific bacterial cells with specific antibodies immobilized on magnetic beads.

U.S. Pat. No. 5,665,582 discloses a method for reversibly anchoring a biological material, such as a plastid, chromosome, nucleic acid, or protein to a solid support for use in an immunoassay.

U.S. Pat. No. 5,821,066 discloses a method of detecting, identifying, and quantifying respiring microorganisms in an immunoassay.

BRIEF SUMMARY OF THE INVENTION

The present invention provides for an immunogen comprising outer membrane complexes from multiple strains of

*C. jejuni* and *C. coli*, the immunogen inducing an immune response in animals, such as mice, enhancing the production of hybridomas specific for *C. jejuni* and *C. coli* epitopes, wherein the immunogen induces a broad range of antibodies against many outer membrane molecules of *C. jejuni* and *C. coli*, but not against other gram-negative enteric bacteria or non-*jejuni/coli* Campylobacter. Monoclonal antibodies of the present invention made by using such an immunogen are specific for epitopes expressed on *C. jejuni* and *C. coli*, wherein the monoclonal antibody binds the *C. jejuni* and *C. coli* porin protein or carbohydrate bound to porin protein, the porin comprising the 45 kD and 35 kD monomeric forms and the trimeric form of the porin. The invention also provides for monoclonal antibodies which bind specifically to a 43 kD protein expressed only on *C. jejuni* strains, or to carbohydrate bound to a 43 kD protein expressed only on *C. jejuni* strains.

The invention provides for a method of testing a sample for the presence of *C. jejuni* and/or *C. coli* comprising the steps of:

(a) exposing a sample suspected of containing *C. jejuni* and/or *C. coli* to a MAb which specifically binds *C. jejuni* and *C. coli*;

(b) detecting MAb-antigen binding, said binding being indicative of the presence of *C. jejuni* and/or *C. coli* in said sample; and (c) capturing *C. jejuni* or *C. coli* with MAb-conjugated-magnetic beads or MAb-conjugated-polystyrene beads or MAb conjugated or bound to a solid matrix, and detection of bound *C. jejuni* or *C. coli* with a method selected from: a second specific MAb, a PCR-specific assay, mass spectrometry (MALDI-TOF), reporter phage specific for *C. jejuni* or *C. coli*, optical sensing, or electronic sensing.

The invention also provides for a method of immunizing animals by:

(a) preparing an immunogenic complex by isolating outer membrane complexes from at least two Campylobacter strains selected from at least one *C. jejuni* and at least one *C. coli*;

(b) pooling in approximately equivalent concentrations of the Campylobacter outer membrane complexes;

(c) immunizing animals intravenously; and (d) screening antisera for Campylobacter antibody production.

The invention provides further for a method of making a monoclonal antibody specific for epitopes expressed on the outer membranes of *C. jejuni* and *C. coli*, wherein the monoclonal antibody binds a *C. jejuni* and *C. coli* porin protein or a porin protein-carbohydrate complex, the method comprising:

(a) preparing an immunogenic complex by isolating outer membrane complexes from at least two Campylobacter strains selected from the group consisting of *C. jejuni* and *C. coli*;

(b) pooling in approximately equivalent concentrations of the Campylobacter outer membrane complexes;

(c) immunizing animals intravenously;

(d) screening antisera for Campylobacter antibody production;

(e) fusing isolated spleen cells from animals positive for Campylobacter antibody production and myeloma cells;

(f) isolating hybridomas making antibodies that bind Campylobacter; and (g) screening and identifying monoclonal antibodies that bind Campylobacter.

The present invention further provides for monoclonal antibodies made by such a method, wherein the MAb binds common epitopes of *C. jejuni* and *C. coli*.

The present invention is summarized further in that monoclonal antibodies specific for (1) unique epitopes of *C. jejuni* and (2) epitopes conserved between *C. jejuni* and *C. coli* outer membranes are produced by hybridomas formed by the fusion of cells from a mouse myeloma line and spleen cells from a mouse previously immunized with a mixture of outer membrane complexes (OMC) isolated from eight LPS serotype strains and two poultry strains of *C. jejuni* and *C. coli*. The monoclonal antibody designated as C731 is characterized in that it reacts with a protein having a molecular weight of approximately 44 kilodaltons and a carbohydrate moiety. The monoclonal antibody designated as C740 is characterized in that it reacts with a protein having a molecular weight of approximately 43 to 44 kilodaltons and a carbohydrate moiety.

The present invention is further directed to a process for producing monoclonal antibodies against Campylobacters comprising propagating a hybridoma formed by fusing a cell capable of producing antibodies against (1) *C. jejuni* or (2) *C. jejuni* and *C. coli* with a myeloma cell and harvesting the antibodies produced by the hybridoma.

It is an object of the present invention to produce monoclonal antibodies that are highly specific for (1) specific or distinct epitopes of *C. jejuni* and (2) epitopes shared between *C. jejuni* and *C. coli* outer membranes.

Another object of the present invention is to develop tests using monoclonal antibodies to assay for *C. jejuni* and *C. coli* isolated in pure culture and in clinical, food, and water samples.

It is further an object of the present invention to develop immunoassays for the detection of Campylobacter in food and in clinical specimens.

Another object of the present invention is to develop a procedure to isolate *C. jejuni* and *C. coli* from foods or other samples and to determine the prevalence of the organisms in the samples.

It is another object of the present invention to detect a neo-epitope of the outer membrane of *C. jejuni*, the neo-epitope defined here as an antigenic epitope comprising a porin protein-carbohydrate complex, wherein the neo-epitope is specific for *C. jejuni* and does not cross-react with other Campylobacters.

Because of their high specificity, the monoclonal antibodies may be a useful reagent for the detection of *C. jejuni* and/or *C. coli* in foods, clinical specimens, or in situ localization of the bacteria. The antibodies of the present invention may be used further to monitor environmental and/or waste water or various facilities for *C. jejuni* and/or *C. coli* contamination. The testing procedure would include, for example, enzyme-linked immunoassays (ELISAs), immunomagnetic capture, radioimmune assays, biosensor assays and other immunoassays including, but not limited to microscopic methods.

The monoclonal antibodies of the present invention may be used singly or in combination, such as in a cocktail mixture, to detect specific Campylobacter species, as neutralizing antibodies, or in a composition comprising one or more antibodies to be used in administering passive immunity to humans, livestock, poultry, or other animals.

The antibodies may be used further in side-by-side assays to determine whether the samples react only with the antibodies specific for both *C. jejuni* and *C. coli* or whether they react only with the antibodies that are specific for *C. jejuni* alone.

Another object of the invention is to provide an immunogen comprising outer membrane complexes from multiple strains of C. jejuni used as a vaccine which induces high levels of specific antibodies directed against C. jejuni and which protects against C. jejuni infection in humans, livestock, poultry, or other animals.

An additional object of the invention is to provide an immunogen comprising outer membrane complexes from multiple strains of C. jejuni and C. coli used as a vaccine which induces high levels of specific antibodies directed against both C. jejuni and C. coli and which protects against C. jejuni and C. coli infection in humans, livestock, poultry, or other animals.

Other objects and advantages of the invention will be apparent from the following detailed description and figures setting forth the preferred embodiment of the invention.

BRIEF DESCRIPTION OF THE DRAWINGS

FIG. 1A and FIG. 1B: MAbs C731 and C740 were identified as specific for Cj and Cc, and Cj only, respectively. These two MAbs were tested with approximately 120 additional strains (mostly Campylobacter). MAb C731 binds predominantly to a 45 kD protein (FIG. 2); MAb C740 binds predominantly to an approximately 44 kD protein. FIGS. 1C through 1F: The graphs representing other MAb binding results have been ordered from the top left to the bottom right based on their specificities for (a) all or most strains of both Cc and Cj, (b) all or most strains of Cj and many Cc, (c) most strains of Cj, (d) some strains of Cj and Cc, and (e) a few strains of Cj. The binding of biotinylated cholera toxin subunit b (CTb), which is specific for GM1 ganglioside, also is shown (bottom right graph). CTb bound to approximately 30% of the Cj strains tested. Cj has been shown to express a variety of ganglioside-like lipopolysaccharide (LPS) structures, including a GM1-like LPS [G. O. Aspinall, et al. *Biochem.* 33, 241 (1994), A. P. Moran, et al. *FEMS Microbiol. Lett.* 16, 105 (1996).].

FIGS. 5(A and B) shows a nitrocellulose blot of Cj and Cc OMC stained for carbohydrate. Molecules in Cj OMC were separated by SDS-PAGE on a 10% gel, blotted to nitrocellulose, then probed with MAbs and lectins.

FIGS. 10(A through D) shows the qualitative results of binding of MAbs by ELISA to each of the bacteria represented in the immunogen for Fusion 1. The bacteria used as antigen in the ELISA are listed as *Campylobacter jejuni* (Cj) or *Campylobacter coli* (Cc) and the Penner LPS serotype strains (O:1, O:2, O:3, O:4, O:19, O:23, O:30, O:36) are designated.

FIGS. 11(A through K) shows the qualitative results of binding of MAbs by ELISA to each of the bacteria represented in the immunogen for Fusion 2. The antigens tested and LPS serotype designation are the same as for FIG. 10.

FIG. 12A shows immunoreactivity of monoclonal antibodies C731. C736, C775, C777, C779. C791, C810, and C785.

DETAILED DESCRIPTION OF THE INVENTION

Figure 1:
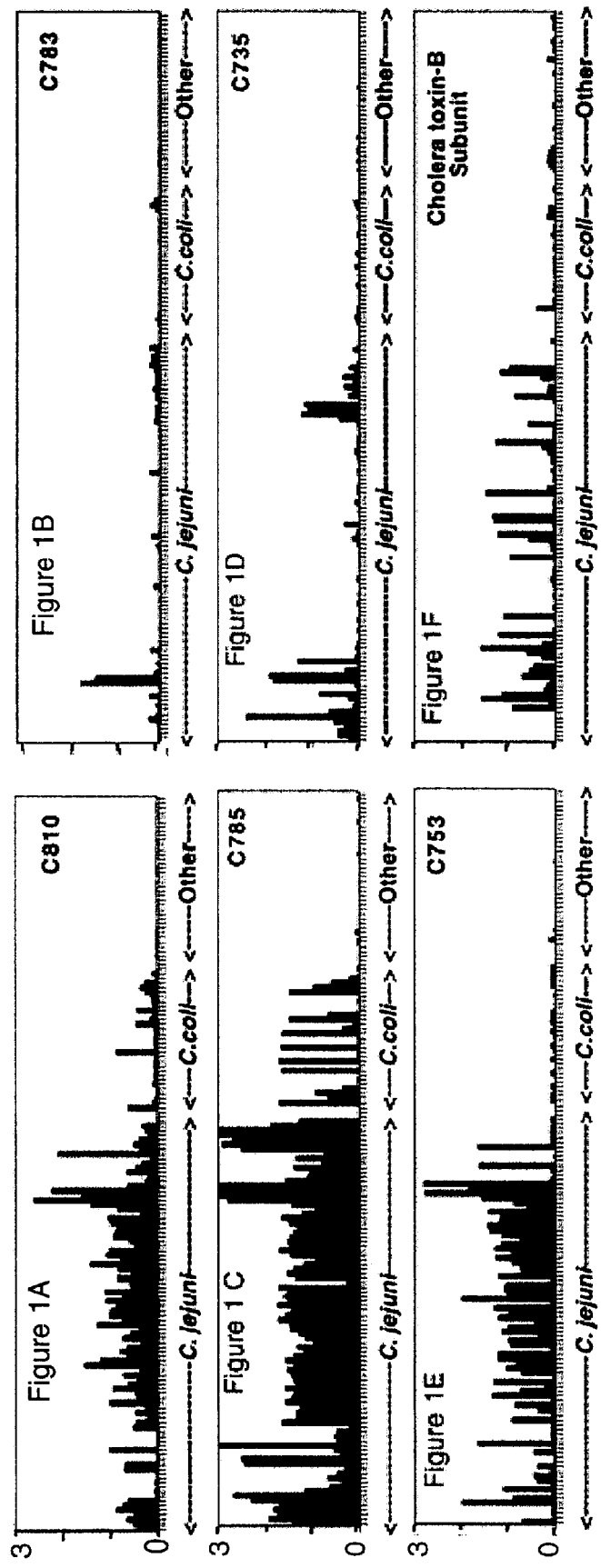
FIGS. 1(A through F) shows the binding of MAbs in an ELISA to Campylobacter and other Gram-negative species of bacteria. A dilution of each of the MAbs was added to microtiter wells containing dried bacterial cells and the binding of MAb was detected with an alkaline phosphatase-conjugated goat anti-mouse IgG secondary antibody and substrate. MAbs were tested for binding to various strains of bacteria (X-axis) in an ELISA. The binding activity ($OD_{405}$) of a similar dilution of each antibody was determined (Y-axis). All MAbs were assayed initially with approximately 120 strains of bacteria.

Before the present antibodies, assays, and methods for producing and using such are disclosed and described, it is to be understood that this invention is not limited to particular antibodies, assays, or methods, as they may vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can antibodies, assays, or methods, as they may vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated herein by reference to disclose and describe the methods and/or materials in connection with which they are cited.

MAb C731, which recognizes both *C. jejuni* and *C. coli*, was recloned and renamed C818. MAb C818 was deposited under the Budapest Treaty with ATCC (Mannassas, Va.) on Feb. 23, 1999, verified to be viable on Mar. 12, 1999, and has been accorded ATCC Designation HB-12651.

MAb C740, which specifically recognizes only *C. jejuni*, was recloned and renamed C825. MAb C825 was deposited under the Budapest Treaty with ATCC (Mannassas, Va.) on Feb. 23, 1999, verified to be viable on Mar. 12, 1999, and has been accorded ATCC Designation HB-12652.

MAb 791, which specifically recognizes *C. jejuni* and *C. coli*, was deposited tinder the Budapest Treaty with ATCC (Mannassas, Va.) on Aug. 3, 2000; verified to be viable on Sep. 22, 2000; and has been accorded ATCC Designation PTA-2327.

Permanence of the deposits and ready accessibility thereto is provided in accordance with U.S. patent law, the Budapest Treaty, and other applicable laws and regulations. The deposits will be accessible to the public on and after the date of issuance of any U.S. patent arising from the present patent application, which refers to the deposits. All restrictions upon availability of the deposited monoclonal antibodies will be irrevocably removed upon granting of any U.S. patent arising from the present application.

The present invention provides for an immunogen comprising outer membrane complex from multiple strains of *C. jejuni* and *C. coli*, the immunogen inducing an immune response in animals, mice in particular, enhancing the production of hybridomas specific for *C. jejuni* and *C. coli* epitopes, wherein the immunogen induces a broad range of antibodies against many outer membrane molecules of *C. jejuni* and *C. coli*, but not against other gram-negative enteric bacteria or non-*jejuni/coli* Campylobacter. The immunogen may comprise outer membrane complexes from two or more strains of *C. jejuni* and *C. coli*, preferably from two to ten strains of *C. jejuni* and *C. coli*, more preferably from five to ten strains, in any combination thereof. The immunogen may be made from outer membrane complexes from two, three, four, five, six, seven, eight, nine, ten, or more strains of *C. jejuni* and *C. coli*, in any combination. The immunogen may further comprise outer membrane complexes from cue or more environmental *C. jejuni* and/or *C. coli* strains isolated from commercially available chickens from the supermarket. In the most preferred embodiment, the immunogen comprises outer membrane complexes from seven strains of *C. jejuni* and one strain of *C. coli* and two environmental *C. jejuni* and or *C. coli* strains isolated from commercially available chickens from the supermarket Monoclonal antibodies of the present invention made by using such an immunogen are specific for epitopes expressed on *C. jejuni* and *C. coli*, wherein said monoclonal antibody binds the *C. jejuni* and *C. coli* porin protein or carbohydrate bound to porin protein, the porin comprising the 45 kD and 35 kD monomeric forms and the trimeric form of the porin.

The invention also provides for monoclonal antibodies which bind specifically to a 43 kD protein expressed only on *C. jejuni* strains, or to carbohydrate bound to a 43 kD protein expressed only on *C. jejuni* strains.

The invention provides for a method of testing a sample for the presence of *C. jejuni* and/or *C. coli* comprising the steps of:
  (a) exposing a sample suspected of containing *C. jejuni* and/or *C. coli* to MAb which specifically binds *C. jejuni* and *C. coli*;
  (b) detecting MAb-antigen binding, said binding being indicative of the presence of *C. jejuni* and/or *C. coli* in said sample; and
  (c) capturing *C. jejuni* or *C. coli* with MAb-conjugated-magnetic beads or MAb-conjugated-polystyrene beads or MAb conjugated or bound to a solid matrix, and detection of bound *C. jejuni* or *C. coli* with: a second specific MAb, a PCR-specific assay, mass spectrometry (MALDI-TOF), reporter phage specific for *C. jejuni* or *C. coli*, optical sensing, or electronic sensing.

The method of testing is described further wherein the sample is selected from the group consisting of poultry, swine and bovine carcasses, tissues and manure; animal production (farm) or processing water and equipment; biofilms on surfaces of animal carcasses, cells, tissues, production equipment or processing equipment; clinical samples (for example, feces or blood); fruit and vegetables; and fruit and vegetable irrigation and processing water.

The invention also provides for a method of immunizing animals by:
  (a) preparing an immunogenic complex by isolating outer membrane complexes from at least two Campylobacter strains selected from the group consisting of *C. jejuni* and *C. coli*;
  (b) pooling in approximately equivalent concentrations of the Campylobacter outer membrane complexes;
  (c) immunizing animals intravenously; and (d) screening antisera for Campylobacter antibody production.

The invention also provides for a method of making monoclonal antibodies specific for epitopes expressed on the outer membranes of *C. jejuni* and *C. coli*, wherein said monoclonal antibody binds a *C. jejuni* and *C. coli* porin protein or a porin protein-carbohydrate complex, the method comprising:

(a) preparing an immunogenic complex by isolating outer membrane complexes from at least two Campylobacter strains selected from *C. jejuni* or *C. coli*;

(b) pooling in approximately equivalent concentrations of the Campylobacter outer membrane complexes;

(c) immunizing animals intravenously;

(d) screening antisera for Campylobacter antibody production;

(e) fusing isolated spleen cells from animals positive for Campylobacter antibody production and myeloma cells;

(f) isolating hybridomas making antibodies that bind Campylobacter; and (g) screening and identifying monoclonal antibodies that bind Campylobacter.

The method further provides an immunogen, which additionally comprises Campylobacter strains isolated in an approximately 1 M NaCl wash of fresh chicken epidermis.

The present invention also provides for monoclonal antibodies, made by such a method, that bind only *Campylobacter jejuni*.

The present invention further provides for monoclonal antibodies, made by such a method, that bind common epitopes of *C. jejuni* and *C. coli*.

More specifically, the present invention is drawn to a monoclonal antibody made by such a method and is designated as C731, recloned and renamed as C818, and deposited as ATCC HB-12651.

The invention also provides for a monoclonal antibody made by such a method and is designated as C740, recloned and renamed as C825, and deposited as ATCC HB-12652.

The present invention provides for the production of monoclonal antibodies that are highly specific for (1) specific or unique epitopes of *C. jejuni* and (2) epitopes shared between *C. jejuni* and *C. coli* outer membranes.

The present invention provides for tests using monoclonal antibodies to assay for *C. jejuni* and *C. coli* isolated in pure culture and in clinical, food, and water samples.

The present invention also provides immunoassays for the detection of Campylobacter in food, water, and in clinical specimens.

The present invention provides procedures to isolate *C. jejuni* and *C. coli* from foods or other samples and to determine the prevalence of the organisms in the samples.

Because of its high specificity, the monoclonal antibodies may be a useful reagent for the detection of *C. jejuni* and/or *C. coli* in foods, clinical specimens, or in situ localization of the bacteria. The antibodies of the present invention may be used further to monitor environmental and/or waste water or various facilities for *C. jejuni* and/or *C. coli* contamination. The testing procedure would include, for example, enzyme-linked immunoassays (ELISAs), immunomagnetic capture, radioimmune assays, biosensor assays and other immunoassays including, but not limited to immunomicroscopy.

The monoclonal antibodies of the present invention may be used singly or in combination, such as in a cocktail mixture, (1) to detect specific Campylobacter species, (2) as neutralizing antibodies, or (3) in a composition comprising one or more antibodies to be used in administering passive immunity to humans, livestock, poultry, or other animals.

The antibodies may be used further in side-by-side assays to determine whether the samples react only with the antibodies specific for both *C. jejuni* and *C. coli* or whether they react only with the antibodies that are specific for *C. jejuni* alone.

An immunogen comprising outer membrane complexes from multiple strains of *C. jejuni* may be used as a vaccine which induces high levels of specific antibodies directed against *C. jejuni* and which protects against *C. jejuni* infection in humans, livestock, poultry, or other animals.

An immunogen comprising outer membrane complexes from multiple strains of *C. jejuni* and *C. coli* may be used to as a vaccine which induces high levels of specific antibodies directed against both *C. jejuni* and *C. coli* and which protects against *C. jejuni* and *C. coli* infection in humans, livestock, poultry, or other animals.

The immunogens of the present invention may also be used to assay the blood of test subjects to determine exposure to *C. jejuni* or *C. coli*.

The scope of the present invention is not limited to the uses discussed above or to the specific examples described below.

Preparation of Immunogen

Campylobacter is a phenotypically diverse organism. This is reflected by the large number of heat stable (Penner LPS system) (Preston and Penner, 1987) and heat sensitive (Lior system) (Suzuki et al., 1993) serotypes that have been identified. Therefore, the type of immunogen is crucial to producing MAbs that recognize an epitope specific to pathogenic Cj strains, and an epitope expressed on all strains of this subspecies.

The immunogen was prepared with outer membrane complexes prepared from strains representative of the most common Cjj and Cc isolated from humans and a Cjj strain isolated from poultry. Outer membrane complexes of ten strains were pooled. These strains represented seven Cjj Penner lipopolysaccharide (LPS) serotype reference strains (O1, O2, O3, O4, O19, O23, O36) (Preston and Penner, 1989; Preston and Penner, 1987), one Cc Penner lipopolysaccharide (LPS) serotype reference strain (O30) (Preston and Penner, 1989; Preston and Penner, 1987), and two strains isolated from a chicken purchased in a local retail market (RM1221 and RM 1222; see below). The LPS reference strains were grown on Brucella Agar with supplements (BA) (Vanderzant and Splittstoesser, 1992). Strains RM 1221 and 1222 were isolated from chicken tissue by a procedure modified from those reported previously (Acuff, 1992). A method was developed to obtain a strain more likely to be adapted to attachment to chicken epidermis. A small "pocket" was formed into a sample of skin cut from the breast of a retail chicken, approximately 1 ml of 1 M NaCl was added to the pocket and drawn in and out of a pipet tip 3 times, and the wash solution was centrifuged at 14,000 rpm for 30 sec. The pellet was resuspended in 200 µl of Preston Selective Enrichment Broth (PSEB) (Uyttendaele and Debevere, 1996) and added to 10 ml of additional PSEB in a petri dish. The dish was incubated in ajar for 1 day at 42 C. under microaerophilic conditions (85% $N_2$, 10% $CO_2$, and 5% $O_2$) with shaking (20–25 rpm). One loopful of the enriched broth was streaked on blood-free Campylobacter Charcoal Differential Agar (CCDA) (Acuff, 1992) and incubated for 24 to 48 h under microaerophilic conditions. Two different colony morphologies were noted: strain RM 1221 which grew as a non-isolated "swarming and glistening" colony, typical of the majority of the growth on the plate and most Cjj strains isolated from chicken; and strain RM1222, an isogenic population variant (confirmed by pulsed field gel electrophoresis (PFGE)) which grew as an isolated colony with a "dry" appearance.

Each of the Campylobacter strains was subcultured onto approximately 5 to 10 BA plates and grown for 2 days at 42 C. in a microaerophilic atmosphere. The bacteria were harvested from plates with sterile plastic loops and suspended in approximately 20 ml of 0.1 M Tris—0.01M EDTA—0.15M NaCl, pH 8.0 (TEN buffer). The bacteria were vortexed well to suspend the bacteria, then passed through a 26 g needle on a syringe. The bacterial suspension was added to a clean stainless steel Omnimixer jar (Sorvall) and the suspension was mixed with an Omnimixer for 30 sec. The suspension was incubated in a 65 C. water bath for 1 hour. The suspension then was mixed with an Omnimixer for 5 minutes on ice (this step shears the bacterial outer membranes from most of the peptidoglycan layer of the bacteria). The suspension was added to a 37.5 ml Oakridge centrifuge tube and centrifuge at approximately 10,000× g for 20 minutes. The supernatant was transferred to another tube. An amount of TEN buffer equal to the first extraction was added to the pellet, and the pellet was suspended, heated and mixed as described above. The supernatants were pooled and centrifuged again at approximately 10,000× g to pellet particulates. The supernatant was centrifuged at 50,000 rpm in an ultracentrifuge (Ti70 rotor, Beckman L8) for 2 hours. The supernatant was discarded and the inside of the tube was washed carefully with distilled water without disturbing the pellet. The pellet was suspended in approximately 2 to 3 ml pyrogen-free (PF)-water (18 megOhm resistance), vortexed vigorously to suspend, and then passed through a 26 g needle to suspend the small clumps of outer membrane more fully. The ultracentifuge tube containing the suspended outer membrane complex (OMC) was filled with PF-water, and the tube was ultracentrifuged at 50,000 rpm again for 2 hours. The amber-colored pellet was suspended in 1 to 2 ml PF-water.

The presence of protein, lipopolysaccharide (LPS) and lipopolysaccharide (LOS) in the OMC preparation was confirmed by SDS-polyacrylamide gel electrophoresis (both 7.5 and 15%) and Coomassie and protein silver staining, and LPS silver staining. The protein concentration of OMC was determined with a bicinchoninic acid protein assay kit (Pierce, Inc). OMC samples were stored at −20 C until further use.

Immunizations

Each OMC of the ten strains of Campylobacter was pooled in an amount resulting in approximately equivalent concentrations of OMC protein for each strain. LOS was present in significant amounts in the OMC as evidenced by silver stains of the gel. The mixture was diluted with saline to a final protein concentration of 200 µg/ml. All immunizations using the OMC mixture were done intravenously and without any adjuvant. The complex of LOS/LPS (mitogenic) with protein in OMC was effective as an adjuvant and in inducing specific antibodies in mice.

BALB/c mice were immunized with three or four intravenous inoculations at approximately 2-week intervals with 50 to 60 µl of the mixed OMC (first dose of 10 µg protein; subsequent doses of 20 µg protein). About 1 week after the 2nd inoculation, antibody production was assessed in an enzyme-linked immunosorbent assay (ELISA) with dilutions of mouse sera (details below).

Preparation of ELISA Plates Using Bacterial Cells

An ELISA method was developed for the detection and characterization of anti-Campylobacter antibodies with whole bacterial cells dried on ELISA plates. Campylobacter strains were cultured on agar plates, the bacteria were harvested, then suspended in phosphate buffered saline (PBS: 10 mM sodium phosphate, 150 mM NaCl, pH 7.4) to an absorbance of 0.2 at 620 nm. Seventy µL of the suspension was added to polystyrene assay wells (Immulon II, Dynatech, Chantilly, Va. or Maxisorp, Nunc, Roskilde, Denmark). The plates were allowed to dry by incubating them for 18 to 24 hours at 37 C, they were washed 3 times with Tris-HCl buffered saline containing 1% Tween 20 (TBS-Tween) or PBS-Tween (diluents), then with a final rinse of PF water. Non-specific binding sites on the wells were blocked by adding 200 µl of 3% bovine serum albumin in TBS-Tween (BSA-TBS-Tween), then incubating the plate at room temperature (RT) for 1 hr. The plates were rinsed and washed as described above and used immediately, or they were stored in a desiccator at 4 C. for later use. Other ELISA plates, blocking buffers and diluents were tested with similar results.

ELISA Method to Identify Anti-Campylobacter Antibodies in Hybridoma Supernatants Samples of culture supernatants containing hybridoma antibody were diluted in TBS-Tween as described above. Samples of 100 µl were added to immobilized Campylobacter in the wells, usually in duplicate, and the wells were incubated with gentle shaking for 1–2 hours at RT. Wells were emptied, then washed and rinsed with water. Bound antibody was detected by adding 100 µl of alkaline phosphatase (AP)-conjugated rabbit anti-mouse Ig diluted 1:1000 to 1:2000 in ELISA diluent, incubating the wells for 1 hour with shaking, then washing and rinsing the wells with water. Next, 100 µl of p-nitrophenylphosphate (pNPP) (1 mM pNPP in 10 mM diethanolamine, 0.5 mM $MgCl_2$, pH 9.5) was added, and the absorbance at 405 nm was determined on a plate reader. Assays were generally read after 30 minutes. In some experiments, screening assays were conducted with horseradish peroxidase-conjugated anti-mouse Ig reagents (Zymed Laboratories), developed using tetramethylbenzimidine-hydrogen peroxide substrate (ELISA Technologies, Lexington, Ky.), and the reaction was stopped using 0.3 N HCl.

Cell Fusion

Sera from immunized mice were assayed in an ELISA (see method above). Mice producing a high titer of serum antibody against OMC antigen were used for production of MAbs, using a protocol adapted from Oi and Herzenberg (Oi and Herzenberg, 1980). The schedule of immunization is shown in Table 1 below:

TABLE 1

| Day | Procedure | Expt. 1 | Expt. 2 |
| --- | --- | --- | --- |
| 0 | i.v. inoculation | + | + |
| 13 | i.v. inoculation | + | + |
| 29 | i.v. inoculation | + | + |
| 32 | cell fusion | + | − |
| 36 | i.v. inoculation |   | + |
|   | cell fusion |   | + |

A mouse producing anti-OMC antibody by ELISA was selected in each of two fusion experiments and inoculated intravenously with the mixed OMC suspension (100 to 200 µg of protein in PBS) either three (Expt. 1) or four (Expt. 2) days prior to cell fusion 1 or 2, respectively. Equal numbers of immune spleen cells and myelonia cells (P3X63-Ag8.653, Kearney et al., Journal of Immunology 123: 1548–1550 (1979)) were fused by treatment with 50% PEG 1450 (American Type Culture Collection, Manassas, Va.), and the fusion suspension was dispersed into 96-well tissue culture plates, 200 μl/well, at a cell density of 1.5×10⁶ cells/ml. Hybridomas secreting Campylobacter-specific antibody were identified by ELISA (details below). Initial screening of Hybridoma supernatants Fusion culture supernatants were harvested after approximately two weeks growth, diluted (1:5–1:10) in Tris-buffered saline (TBS, 25 mM Tris-Cl, 0.15 M NaCl, pH 7.4) containing 10 mg/mL bovine serum albumin (BSA) and 0.05% Tween-20 (BSA-TBS-Tween) (referred to below as diluent), and applied to Campylobacter-coated assay wells. Each culture was screened on a panel of wells containing each of 10 different Campylobacter strains included in the preparation of the OMC immunogen: (LPS serotypes O1, O2, O3, O4, O19, O23, O30, O36, and isolates RM1221 and RM1222). In these screenings, AP-conjugated rabbit-anti-mouse (IgG+ IgM+IgA) (Zymed Laboratories, South San Francisco, Calif.) was used as labeled reagent and p-nitrophenylphosphate (pNPP) as substrate (1 mM pNPP in 10 mM diethanolamine, 0.5 mM MgCl2. pH 9.5). Positive cultures were identified (typically absorbance greater than 0.5 absorbance units at 405 nm after 30 minutes), using a microplate reader (V-max, Molecular Devices, Menlo Park, Calif.). In some screening assays, the phosphate-buffered saline (0.005 M sodium phosphate, 0.15 M NaCl, pH 70, PBS) was used instead of TBS in the diluent. Variations in buffer components did not appear to affect the results. In addition, horseradish peroxidase was used as label in most subsequent screenings of clones (see below).

Reproducibility of Induction of Anti-Cj and Anti- Cj/Cc MAbs by Immunogen

Approximately 500 wells were screened by ELISA with each of the 10 strains (9 Cjj, 1Cc) used for the OMC immunogen as antigen. Approximately 55% of the Fusion 1 wells (FIGS. 10, A through D) and 26% of the Fusion 2 wells (FIGS. 11, A through K) were positive with at least one of the 10 strains. Most of the wells contained antibody that was positive for multiple strains. Between 6 and 8% of the Fusion 1 and Fusion 2 wells were positive for at least 9 of 10 strains. Many wells contained Cj-specific antibody and many were Cj/Cc-specific in initial ELISA screening. The results obtained for two independent fusion experiments indicated that the mixed OMC was a very effective immunogen for inducing consistently MAbs that recognize: (1) different Campylobacter outer membrane molecules, (2) Cj-specific antigens, (3) antigens common to both Cj and Cc, but not other Campylobacters.

Expansion and Cloning of Hybridomas

Selected cultures were transferred to larger wells as needed and frozen. Selected hybridoma cultures were cloned by limiting dilution. Clones were expanded in culture, permitting harvest of supernatant, freezing of cell lines, and preparation of ascites fluid. Selected lines were recloned in order to improve growth characteristics and to ensure the clonality and stability of cell lines. MAbs were assayed for isotype by ELISA, using isotype-specific antibodies conjugated to horseradish peroxidase (Zymed Laboratories).

Antibody Production in vivo

BALB/c mice were injected with 2,6,10,14-tetramethylpentadecane (Aldrich Chemical Co., St. Louis, Mo.) 10 days and 3 days prior to intraperitoneal inoculation with 6×10⁶ viable hybridoma cells. High-titer ascitic fluid and sera were obtained from most of the mice within 3 weeks of inoculation. Ascitic fluid was tested for antibody activity by ELISA.

Specificity of MAbs

Ascitic fluids positive by ELISA were characterized further for specificity with additional strains of bacteria in ELISA. Approximately 150 strains of Cj, Cc, non-Cj/Cc Campylobacter, Cj subspecies *doylei* (Cjd), Arcobacter, Salmonella, and other Gram-negative enteric bacteria were assayed by ELISA with 21 ascitic fluids produced from different hybridomas. An additional 130 strains were assayed with C731 (anti-Cj/Cc) and C740 (anti-Cj). Human, chicken, turkey, calf and pig isolates were represented among the Cj and Cc strains. Approximately 60 of the Cj and Cc isolates were isolated from turkeys representing 28 locations in the U.S. and were highly diverse genotypically based on unique pulsed gel electrophoresis patterns (not shown). Among the gram-negative enteric isolates were 14 different serotypes of Salmonella spp. and 6 *E. coli* 0157:H7 strains. The results shown in FIG. 1 are a summary of the data from these experiments.

The results of these initial ELISA assays indicated that MAbs C740 and C760 bind to Cjj and Cjd strains, but not to Cc or any other strain tested. C740 and C760 each bound to 92 of 93 (99%) Cjj strains. C740 and C760 were considered likely to be identical hybridomas based on their identical specificity in ELISA and immunoblots and identical IgG isotypes. Therefore, only C740 was analyzed further. MAbs C731, C736, C775, C777, C779, and C791 bind to most Cj and Cc strains, although some differences in the amount and specificity of binding were noted. MAbs C810, C785, and C751 bind to most, but not all Cj and Cc strains. MAb C753 binds to a few Cj strains, and not to Cc strains. The remainder of the MAbs bind to selected strains of Cj and Cc. MAbs C783 and C735 bind only to the chicken-isolated Cj strains included in the immunogen. The number of isolates recognized by MAbs C731, C740 and C753 is shown in Table 2.

TABLE 2

| Species | No. Strains | Number positive with MAb (%): | | |
|---|---|---|---|---|
| | | C731 | C740 | C753[c] |
| Cj | 160 | 160 (100) | 159 (99) | 54 (58) |
| Cc | 70 | 70 (100) | 0 (0) | 0 (0) |
| Cj subspecies *doylei* | 6 | 6 (100) | 6 (100)[a] | 0 (0) |
| Campylobacter, non-*jejuni* and -*coli* | 30 | 0 (0)[b] | 0 (0)[b] | 0 (0) |
| Arcobacter spp. | 14 | 0 (0) | 0 (0) | 0 (0) |
| *Helicobacter pyllorum* | 3 | 0 (0) | 0 (0) | ND |
| Salmonella spp. | 14 | 0 (0) | 0 (0) | 0 (0) |
| Other Gram neg. enterics | 10 | 0 (0) | 0 (0) | 0 (0) |

[a]Binding was lower than with most Cj strains.
[b]Binding was much lower than with Cj or Cc strains: range of OD$_{405}$ values were 0 to 0.15.
[c]For C753, 96 strains of Cj, 32 strains of Cc, 3 strains of Cj *doylei*, and 15 strains of non-Cj/Cc were tested. The number of strains of the other species tested was the same.

None of the 21 MAbs selected for further characterization bound to any strain other than Cj or Cc. Strains of Cjd were assayed also to demonstrate if the antibody is specific for both subspecies of Cj. C740 and C731 bound to 6 strains of Cjd; however, binding was ~50% lower relative to other strains of Cjj. This result suggested that the epitope recognized on Cjd strains is: (i) present, but in lower quantity, (ii) present, but sterically hindered, or (iii) structurally similar and cross-reactive, but not identical. Therefore, the OMC immunogen was effective in inducing MAbs that specifically bind to Cjj, Cjd, and Cc.

Antigenic Regions Recognized by MAbs

Figure 2A:
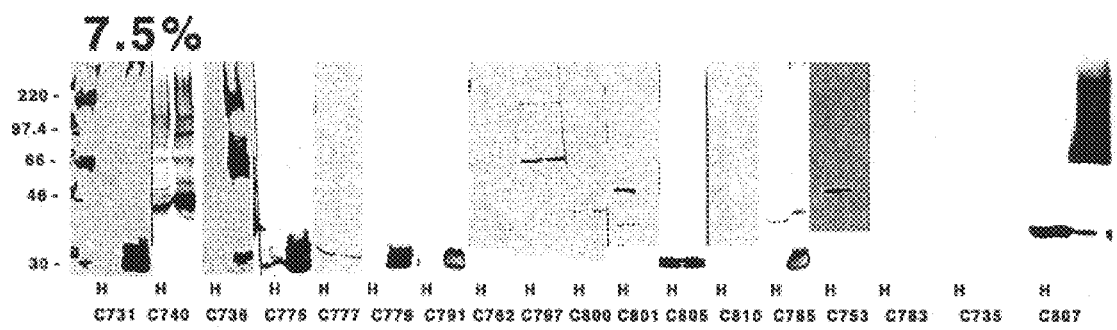
FIGS. 2(A and B) shows immunoblots of MAbs with outer membrane antigens. Molecules in outer membrane preparations (OM) of Cj or Cc were separated by SDS-PAGE on both a 7.5% and 15% gel, blotted to nitrocellulose, then tested with MAbs. Both heated (10 min, 100 C.: "H") and non-heated samples were separated on the 7.5% gel (FIG. 2A); only heated samples were separated on the 15% gel (FIG. 2B). MAb binding was detected with an alkaline-phosphatase-conjugated goat anti-mouse Ig antibody and substrate. MAbs were identified that recognize: (a) epitopes on molecules ranging in size from approximately 18 to 66 Mr; (b) heat stable (see C740, C797, C805) and unstable (see C753, C779, C783, C791) epitopes; (c) heat modifiable proteins, and (d) molecules migrating at multiple $M_r$, especially those in unheated samples (see C731, C740, C736, C775, C779, C805, C807). MAb C731 recognizes the major outer membrane protein (MOMP, porin) of both Cj and Cc (anti-Cj/Cc) (see FIG. 4). The Cj porin has been described previously as a 45 kD protein that migrates in SDS-PAGE gels both as 45 and 35 kD monomers (heat modifiable) [W. Schroder, and I. Moser, *FEMS Microbiol Lett.* 150, 141 (1997), J. -M. Bolla, et al., *J Bacteriol.* 177, 4266 (1995)].
Figure 2B:
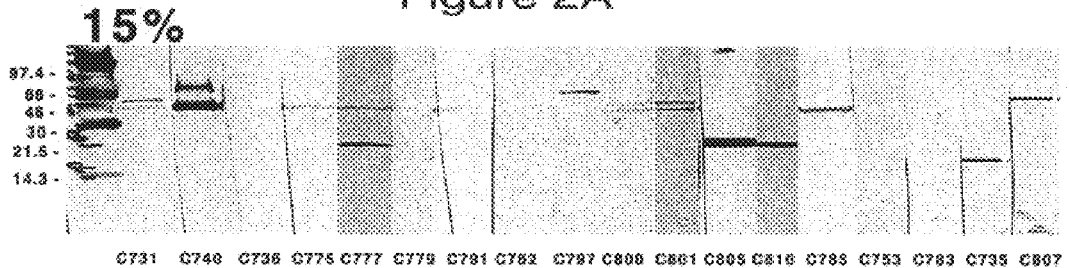

Each of the ascitic fluids was tested to determine the OMC antigen recognized by the MAb by SDS PAGE and immunoblot. OMC's were prepared for SDS-PAGE by mixing 1:1 with gel sample buffer and either heating at 100 C. for 5 min or not heating. Samples were applied to the gel, the gels were electrophoresed and molecules in the gel were transferred to nitrocellulose in a BioRad SemiDry electroblot apparatus. The nitrocellulose was blocked with a blocking solution (0.5% casein-0.01M Tris-HCl-0.031M NaN$_3$-0.15M NaCl) for 1 hr or overnight, 4 C. The lanes containing samples were excised and incubated with a 1:500 to 1:1000 dilution (in casein blocking solution) of ascitic fluid and incubated with shaking for at least 2 hr at RT. The membrane was washed with wash buffer (TBS—0.1% Tween 20—0.1% azide, pH 7.4), an alkaline-phosphatase conjugated goat anti-mouse Ig was added (Zymed), the paper was incubated on a shaker for 1 hr at RT, and then the paper was washed. A substrate solution of BCIP/NBT was added and the blot was incubated on a shaker until bands began to appear. When the intensity of staining was sufficient, the substrate was removed and the paper was washed with water. The approximate Molecular Mass ($M_r$) of bands binding MAbs were determined by reference to standards included on each blot. In some experiments, 7.5%, 10% and 15% gels were used for OMC samples. Sixteen of the 21 ascitic fluids were also tested for binding to electroblotted molecules from both a heated or non-heated OMC separated on a 7.5% SDS-PAGE gel (FIG. 2). Nine or 10 of the MAbs recognized heat-modifiable molecules, presumably proteins. These MAbs bound to the non-heated sample much better than to the heated sample. The heat-modifiability and $M_r$ of the proteins recognized by MAbs C731, C736, C775, C779, C791, and C785 both suggested that these MAbs were specific for the major outer membrane protein (MOMP), or porin, of Cj and Cc (Bolla et al., 1995), a protein comigrating with the porin, or a carbohydrate coupled to the porin. Other MAbs bound to higher or lower Mr proteins.

A summary of the approximate Mr of molecules recognized by the MAbs and their heat-modifiable characteristics are shown in Table 3.

TABLE 3

| Ascites | 1/Dil | Approx. Mr recognized (kD) | Other |
|---|---|---|---|
| C731 | 750 | 35, 45 | porin, heat modifiable, Cj/Cc-specific |
| C735 | 750 | 22 | not heat modifiable |
| C736 | 750 | 32 | porin, heat modifiable |
| C740 | 750 | 35, 43–44 | not heat modifiable, Cj-specific |
| C751 | 750 | 60 | heat modifiable |
| C752 | 750 | 49 | ND |
| C753 | 750 | 35, 45 | porin, heat modifiable |
| C760 | 750 | 35, 43–44 | same hybridoma line as C740 |
| C762 | 750 | 40, 60 | heat unstable |
| C775 | 750 | 33, 45 | heat modifiable |
| C777 | 750 | 24, 51 | not heat modifiable |
| C779 | 750 | 34 | heat modifiable |
| C783 | 750 | 43 | not heat modifiable |
| C785 | 750 | 41 | not heat modifiable |
| C791 | 750 | 32 | heat, modifiable, porin |
| C797 | 750 | 68 | not heat modifiable |
| C800 | 750 | 40 | not heat modifiable |
| C801 | 750 | 45 | porin, heat modifiable |
| C805 | 750 | 32 | not heat modifiable |
| C807 | 750 | 60 | not heat modifiable |
| C810 | 750 | 25 | not heat modifiable |

$M_r$ are approximate values. Multiple values indicate $M_r$ determined with different percentage gels or multiple bands observed for heated and non-heated samples.

Proteins of $M_r$ between approximately 22 and 68 kD were recognized by the 21 MAbs. The $M_r$ recognized has provided clues to the possible identity of some of the proteins recognized; these will be pursued further in future work. However, the major focus of the initial work has been to characterize anti-Cj and anti-Cj/Cc specific MAbs.

Figure 3:
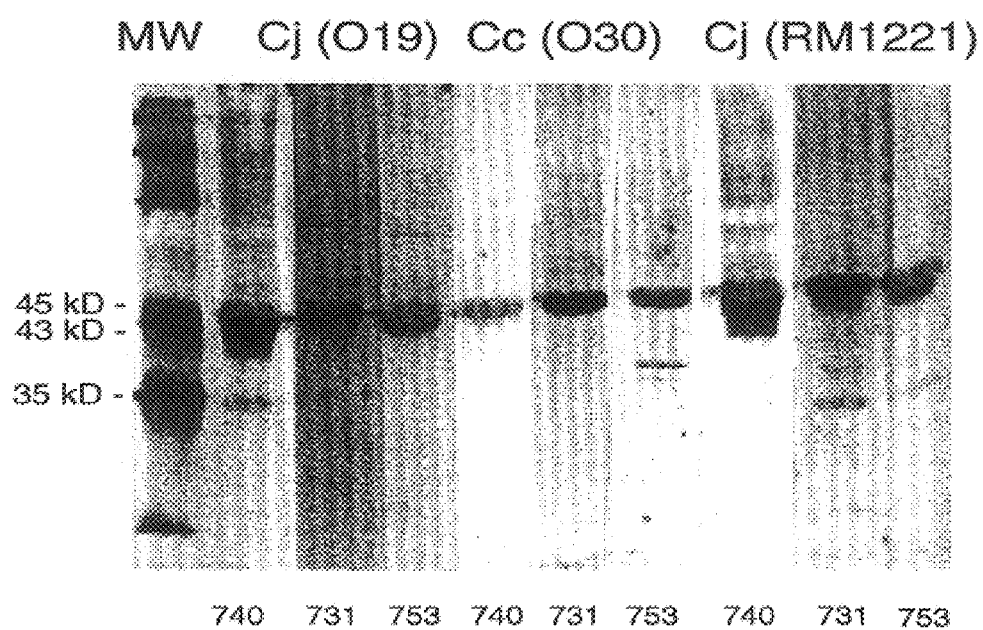
FIG. 3 shows an immunoblot demonstrating the binding of MAbs C731, C740, and C753 to proteins of two Cj strains and a Cc strain. Heated samples were run in a 10% gel.

The specificity of an anti-Cj and two anti-Cj/Cc MAbs were examined more fully. FIG. 3 shows an SDS-PAGE/immunoblot of the binding of MAbs C731, C740 and C753 to proteins of two Cj strains (RM 1049, LPS serotype reference strain O:19, human isolate; and RM 1222, chicken isolate) and a Cc strain (RM1051, LPS serotype reference strain O:30). In this experiment, the incubation time of the development step was extended to reveal maximum binding of the MAbs. Close examination of the immunoblot revealed that the anti-Cj/Cc MAb, C731, bound to the 45 kD MOMP (porin) (Bolla et al., 1995) of each of the strains (FIG. 3). The anti-Cj MAbs C740 and C753. each bound to the porin protein, but they bound more strongly to a diffuse area of the blot of Cj OMC; this is an area at approximately 43–44 kD and lies just below the porin protein. C740 bound much better to the Cj strains than did C753, perhaps reflecting specificity differences observed by ELISA. Coomassie Blue stained predominantly the porin protein. A protein silver stain (BioRad) stained both proteins, but the porin of a Cjj (RM1049) and a Cc (RM 1051) strain stained less well than a second Cjj strain (RM1222). Additional SDS-PAGE/immunoblot experiments with heated and non-heated OMC have confirmed that the 45 kD protein recognized by C731 is indeed the porin protein, based on the binding of the MAb to a 35 kD protein (monomer observed predominantly with non-heated -porin) and a 45 kD protein (monomer) in heated samples, and an approximately 120 kD protein (porin trimer) in unheated and low SDS (0.01%) samples (Bolla et al., 1995). OMC molecules separated by SDS-PAGE were transferred to ProBlott membrane (Perkin Elmer/ABI) and both the C731-positive region and C740-positive region were N-terminal sequenced in an Applied Biosystems sequencer. Thirteen amino acids at the N-terminal end of the 45 kD protein recognized by MAb C731 were identical to those of a Cjj porin described previously (TPLEEAIKDVDVS (SEQ ID NO:1), (Bolla et al., 1995)). Thus, C731 recognizes an epitope shared on the porin proteins of both Cjj and Cc strains. The N-terminal sequence of the protein recognized by MAb C740 was XTPLEE-AIKDV (SEQ ID NO:2).

A sample of OMC was electrophoresed by SDS-PAGE and transferred to nitrocellulose. The blot was incubated with C740 to identify the protein positive for C740. An adjacent slice of nitrocellulose corresponding to the C740-positive protein was analyzed by matrix-assisted laser desorption time-of-flight mass spectrometry. A heterogeneous series of ions with a peak at approximately 45,800 daltons was observed.

Figure 4:
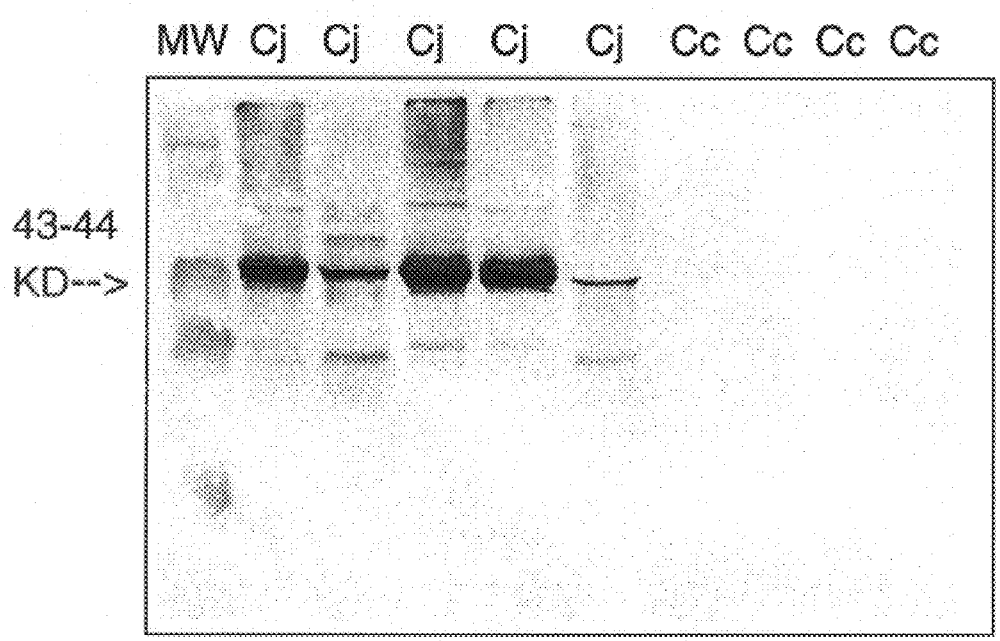
FIG. 4 shows an immunoblot of MAb C740 binding strongly to OMC of 5 Cj strains, but not to any of the OMC of 4 Cc strains. The MAb binds to the 43–44 kD protein best, but also binds to many other proteins of higher and lower Mr and present at lower concentrations.

The specificity of MAb C740 for a 43–44 kD protein of Cjj is demonstrated in FIG. 4. SDS-PAGE/immunoblots of OMC of five Cjj strains and 4 Cc strains show that only Cjj proteins bound MAb C740. The MAb bound to a relatively tight band migrating ahead of the porin protein for two of the Cjj strains, and to a more diffuse band for three of the strains. Minimal binding was observed to the four Cc strains (development time in substrate was less than for FIG. 4).

Only one of approximately 166 Cj tested have not bound MAb C740 in ELISA. A repeat of the ELISA with the one negative strain indicated that C740 bound, but at 10% the binding to most other Cj strains. In previous experiments, it was noted that C740 binding appeared to correlate with hippuricase activity (Hip) detected by a semi-quantitative assay. (Most C. jejuni strains are Hip-positive. C. coli strains are Hip-negative. The Hip assay has been used to discriminate between the two species.) Three Cj strains reported to be Hip-negative (personal communication, John Penner, U. Toronto) were assayed for Hip activity and binding of C740.

Two of 3 strains were Hip-negative, or had Hip below the sensitivity of the assay, but did not bind C740. The third strain had relatively average Hip compared to other Cj strains and was positive for C740 by ELISA. However, further analysis of the two Hip-negative strains by a multiplex PCR assay that identifies Cj and Cc (Harmon et al., 1997) indicated that these two strains were not Cj and that the C740 binding specificity was consistent. A cell lysate preparation of the only authentic C740-negative Cj strain was examined in an SDS-PAGE/immunoblot experiment for binding of C740. C740 bound slightly to the porin (similar to that shown above for other strains; FIG. 3), but little or no binding was observed to the 43 kD protein. Further work will be required to determine definitively the difference between this strain and C740-positive Cj strains.

Carbohydrate Epitopes

Figure 5A:
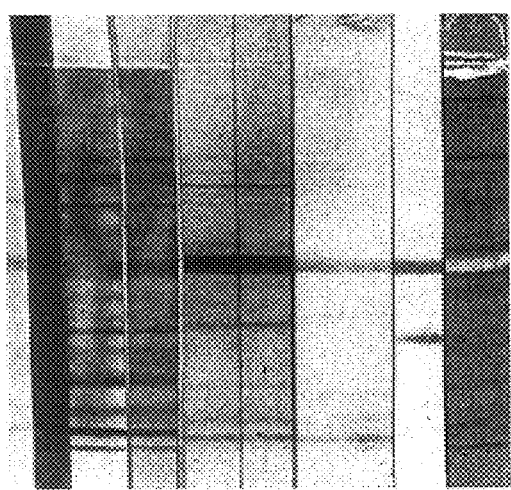
FIG. 5A (Cc strain RM1051 OMC): lane 1: *Limax flavus* agglutinin; lane 2: elderberry bark lectin; lane 3: *Maackia amurensis* agglutinin; lane 4: DIG Glycan stain (experiment 2); lane 5: DIG Glycan stain (experiment 2); lane 6: DIG Glycan stain (experiment 1); lane 7: DIG Glycan stain (experiment 1); lane 8: MAb C731 anti-porin; and lane 9: India ink stain.
Figure 5B:
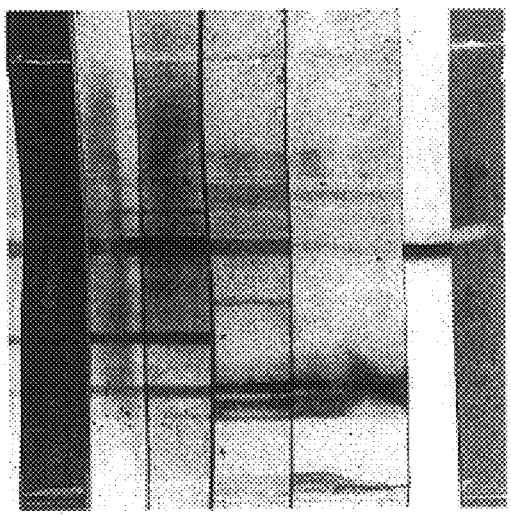
FIG. 5B (Cjj strain RM1222 OMC): lane 1: *Limax flavus* agglutinin; lane 2: elderberry bark lectin; lane 3: *Maackia amurensis* agglutinin; lane 4: DIG Glycan stain (experiment 2); lane 5: DIG Glycan stain (experiment 1); lane 6: DIG Glycan stain (experiment 1); lane 7: MAb C740 anti-porin; and lane 8: India ink stain. The same Cj and Cc OMCs were tested also for the presence of carbohydrate using the DIG Glycan Stain (Boehringer-Mannheim) and lectins and were positive for carbohydrate. An India Ink stain of the blot resulted in a "negative stain" of the porin, further indicating the presence of carbohydrate on porin.

It was determined that the porin protein recognized by a number of the MAbs was glycosylated (FIG. 5). Cjj OMC (strain RM1222) and Cc OMC molecules (strain RM1051) separated by SDS-PAGE and blotted to nitrocellulose were assayed for the presence of carbohydrate with the DIG Glycan Stain (Boehringer-Mannheim, according to the manufacturer's instructions) and with 3 lectins specific for sialic acid glycoconjugates [*Limax flavus* Agglutinin (LFA), *Maackia amurensis* Agglutinin (MAA) and Elderberry Bark Lectin (EBL)]. Both the Cjj and Cc porins were stained with the DIG Glycan stain (lanes 4–7 for Cc strain RM1051 and lanes 4–6 for Cjj strain RM1222). The Cc porin stained darker (left panel lanes 4–5, duplicates, RM1051) than the Cjj porin (right panel, lane 4, RM1222), indicating either a greater amount of carbohydrate present and/or differences in the type of sugars present (e.g. sialic acids are more sensitive to staining than other sugars). In addition, lectins that identify sialic acid residues and sialo-conjugates also bound well to the porin protein (lanes 1–3). LPS bands and flagellin protein of the Cc strain stained for carbohydrate as expected (left panel, lanes 4–7, RM1051 OMC; lanes 4–6, RM1222 OMC). The porin proteins of both the Cjj and Cc stained less with the India Ink compared to other proteins (left panel, lane 9), suggesting possible glycosylation. Both the 45 kD and 35 kD monomeric forms of the Cc porin bound C731 (see left panel, lane 8), however the 35 kD monomer was not stained well (left panel, lanes 4–5). These data indicate that the porin proteins of Cc and Cj (Cj less than Cc) were glycosylated.

OMC treated with proteinase K run in SDS-PAGE and electroblotted to nitrocellulose resulted in no binding of MAb C740 to the 43–44 KD protein, nor to any other area of the blot. This demonstrates that the protein is essential for epitope expression or presentation.

IEF/SDS-PAGE 2D Gel/Immunoblot with Anti-Cj MAb C740

Figure 6:
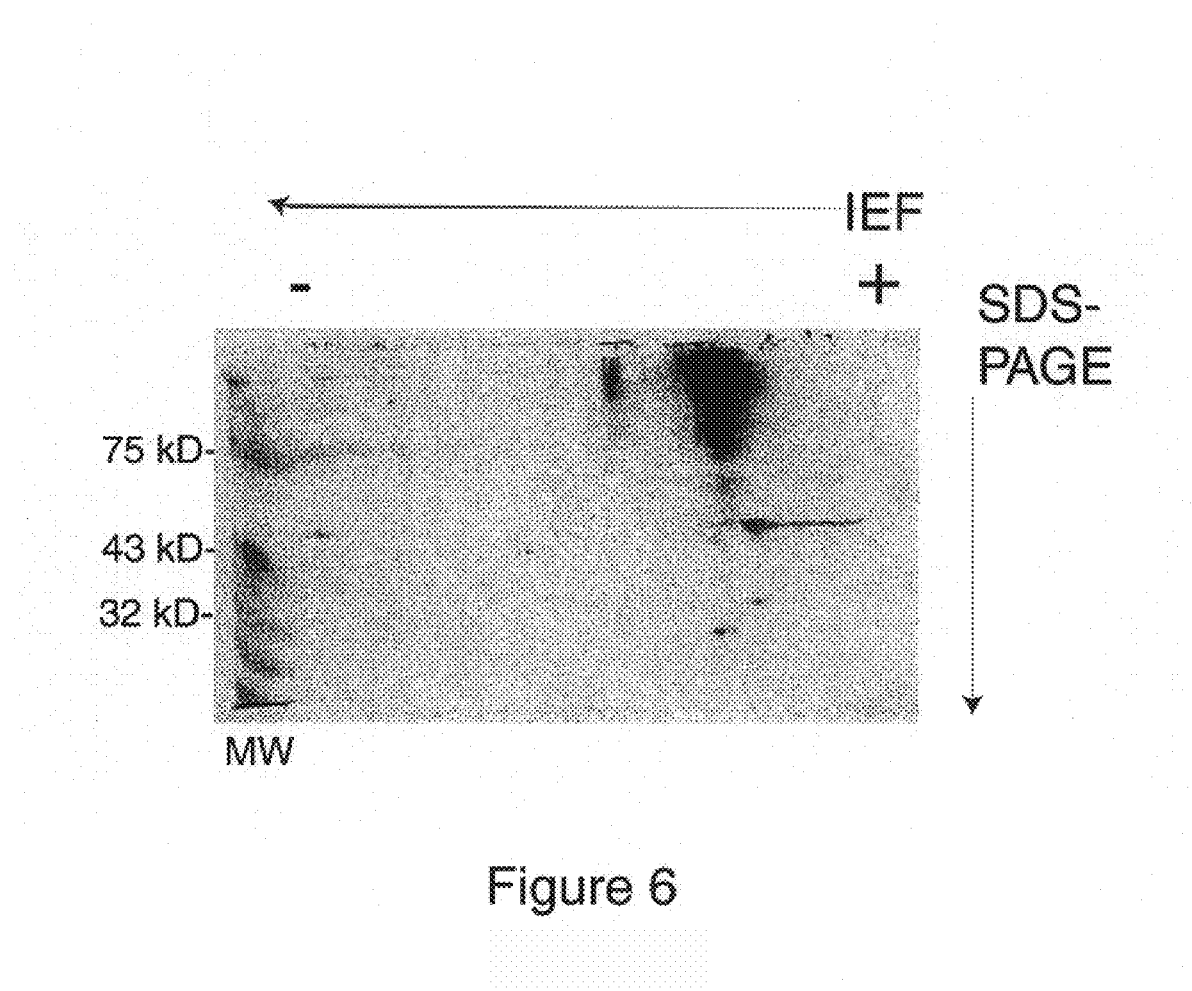
FIG. 6 shows a two-dimensional gel/immunoblot of MAb C740 binding to molecules of Cj OMC. A sample of Cj strain RM1222 OMC was run in an isoelectric focusing gel, then in a second dimension by SDS-PAGE. Molecules in the SDS-PAGE gel were electroblotted to nitrocellulose and tested for binding of MAb C740. The molecules recognized by C740 ran in a broad region at pH 4.

A sample of Cjj strain RM 1222 OMC was prepared in a sample buffer for extracting outer membrane proteins for 2D gel electrophoresis (Molloy et al., 1998). The sample was run in a 2D gel system (isoelectric focusing first dimension, pH 4–7 range gel; 7.5% SDS-PAGE second dimension), transferred to nitrocellulose and tested for binding of the anti-Cj MAb C740 (FIG. 6). Proteins, glycoproteins and other molecules separate by charge in IEF and by relative molecular weight in SDS-PAGE; soluble proteins will appear as spots after silver staining. MAb C740 did not bind to a single protein spot. It bound to a very diffuse area of the blot migrating at greater than 75 kD and less strongly to a series of spots migrating at approximately 43–44 kD. The diffuse area was also stained with the DIG Glycan kit (see paragraph above). These data suggest that a carbohydrate moiety may be associated with the protein recognized by MAb C740, and this association results in a heterogeneous separation of the molecules by IEF. MAb C740 also recognized a series of 43–44 kD monomers that may have different charges and thus different isoelectric points in the IEF gel (FIG. 6, see arrow).

Colony Blot with Anti-Cj MAb C740

Figure 7:
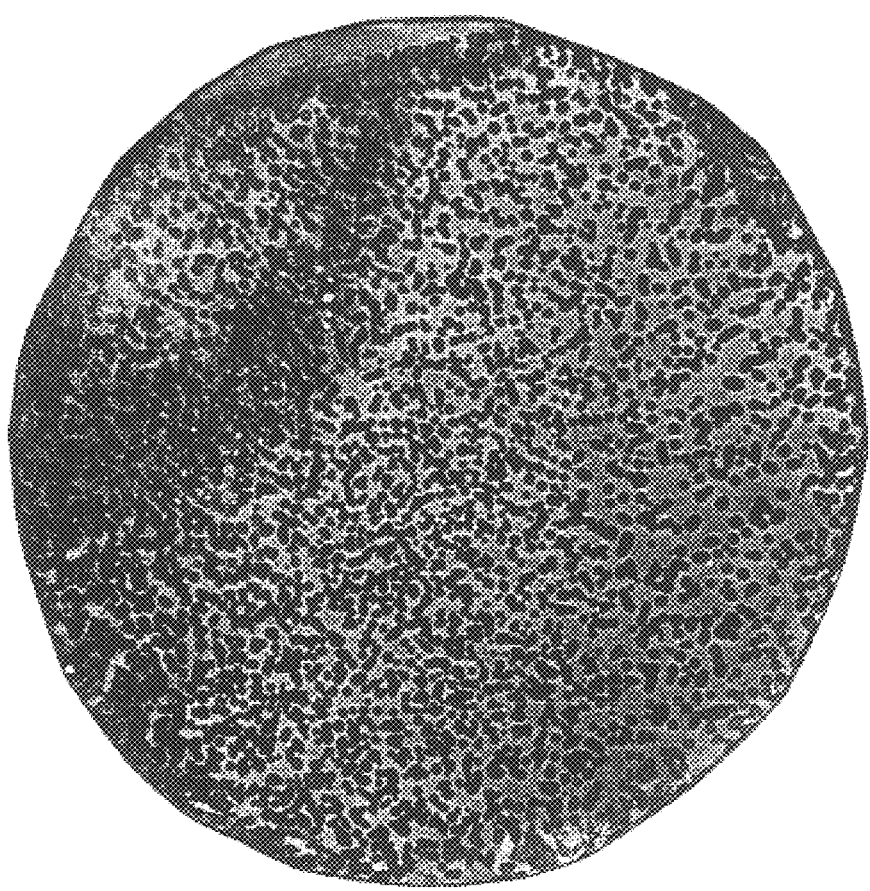
FIG. 7 shows the binding of MAb C740 to colonies of strain Cj strain RM1221. Colonies on an agar plate were transferred to nitrocellulose, dried, then incubated with a dilution of MAb C740. Binding of the MAb was detected with an alkaline phosphatase-conjugated goat anti-mouse IgG and 5-bromo-4-chloro-3-indolyl phosphate/nitro blue tetrazolium or bromochloroindolyl phosphate (BCIP/NBT) substrate.

Colonies of a Cjj strain growing on agar were transferred to a PVDF membrane, dried, then the membrane was incubated with MAb C740 (FIG. 7). Every colony observed (greater than 1000 colonies) bound MAb C740. This result indicates that the epitope recognized on Cjj does not vary phenotypically at a high frequency (less than 0.1%).

Fluorescence Microscopy with Purified C731 and C740 MAbs

The IgG fractions of MAb C731 and C740 were purified from ascitic fluid. The Ig fraction was precipitated from ascitic fluid with ammonium sulfate. The precipitate was solubilized with 20 mM potassium phosphate buffer pH 8.0 and dialyzed against potassium phosphate buffer. The sample was passed through diethylaminoethyl cellulose equilibrated in potassium phosphate buffer (Whatman, Ltd., Maidstone, U.K.) and the unbound fractions containing protein were pooled. The protein concentration was 1 to 1.5 mg/ml. A sample of purified MAb C740 (anti-Cj) was conjugated with Alexa-488 fluorophore (absorbance maximum 491 nm, emission 515; Molecular Probes, Eugene, Oreg.) according to the manufacturers instructions. MAb C731 (anti-Cj/Cc porin) was conjugated with Alexa-546 (absorbance maximum 553 nm, emission 569; Molecular Probes). The two conjugated MAbs were assayed with both plate-bound bacteria and suspended bacteria to examine epitope expression on individual cells (FIG. 8).

Figure 8A:
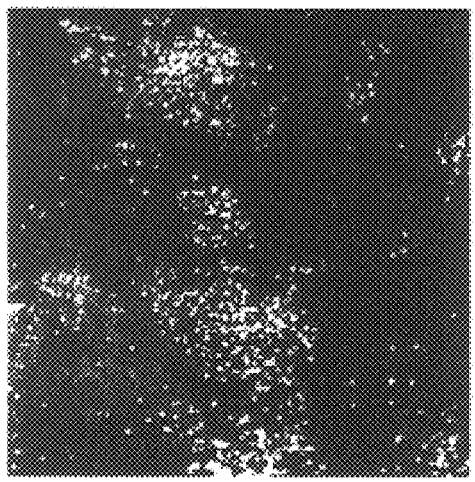
FIGS. 8(A and B) shows the binding of fluorophore-conjugated MAbs C731 and C740 to Cj. The purified MAbs C731 and C740 were conjugated with fluorophores with excitations at 488 nm and 568 nm, respectively.
Figure 8B:
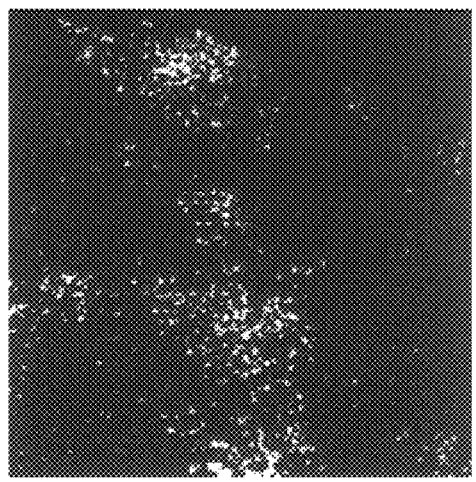

FIG. 8 shows that MAb C731 and MAb C740 bind to most, if not all, of the individual bacteria, but they bind with a subtly different spatial arrangement. C740 appears to bind more closely to the surface of the bacterial cells, whereas C731 (anti-porin) binds further from the surface of the cells. For most cells observed, both MAb-defined proteins were expressed simultaneously. MAbs specific for Cj and Cc specific proteins expressed simultaneously will be advantageous because it will allow development of: (a) of antibody assays using one MAb for capture and another for detection of single organisms, (b) more specific assays, and (c) assays for detecting and discriminating between Cc and Cj.

Fluorescence Microscopy of Chicken Skin with MAb C740

Figure 9:
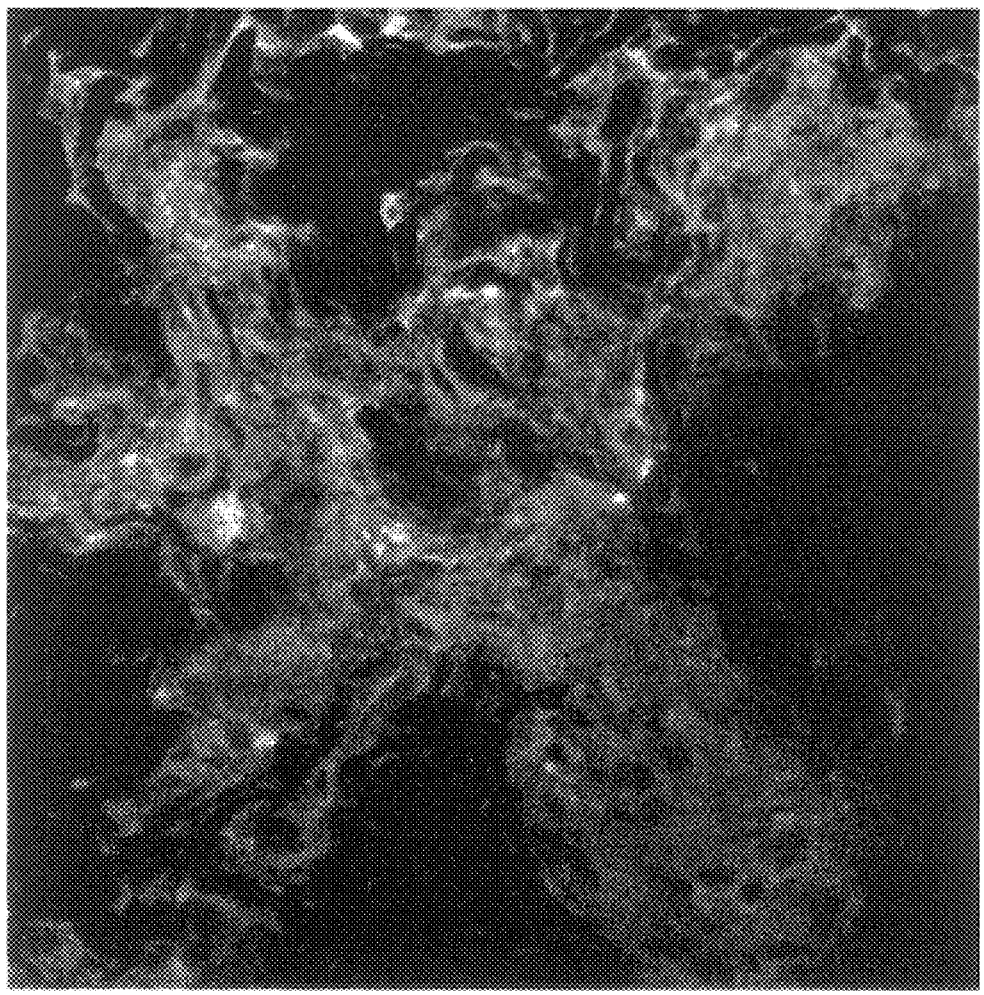
FIG. 9 shows Cj cells present on chicken skin. Retail chicken skin was incubated with MAb C740, then a fluorescent secondary antibody. MAb binding was observed by confocal microscopy.
Figure 12A:
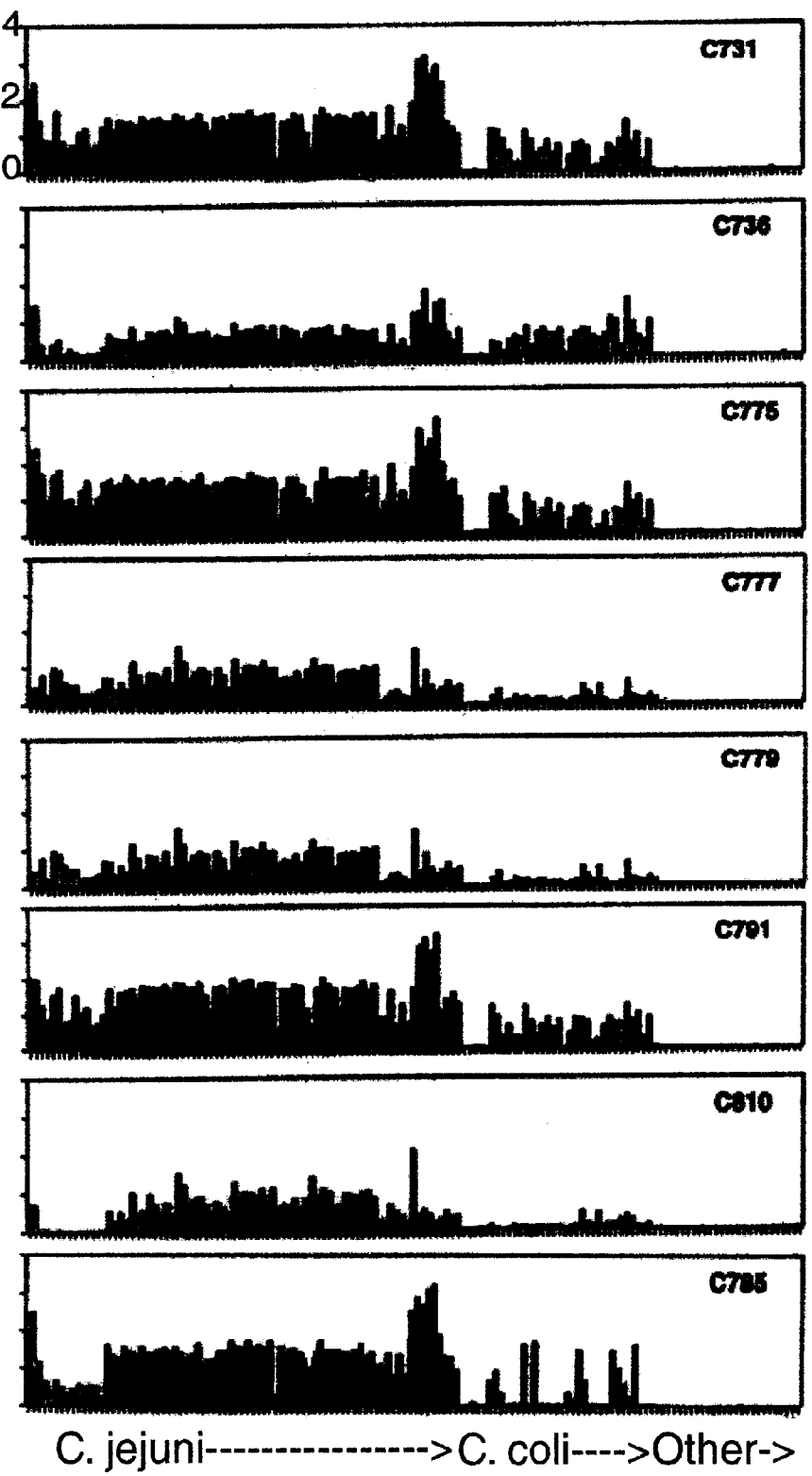
FIGS. 12A & B show the ELISA activity of monoclonal antibodies with Campylobacter and other gram negative species of bacteria.
Figure 12B:
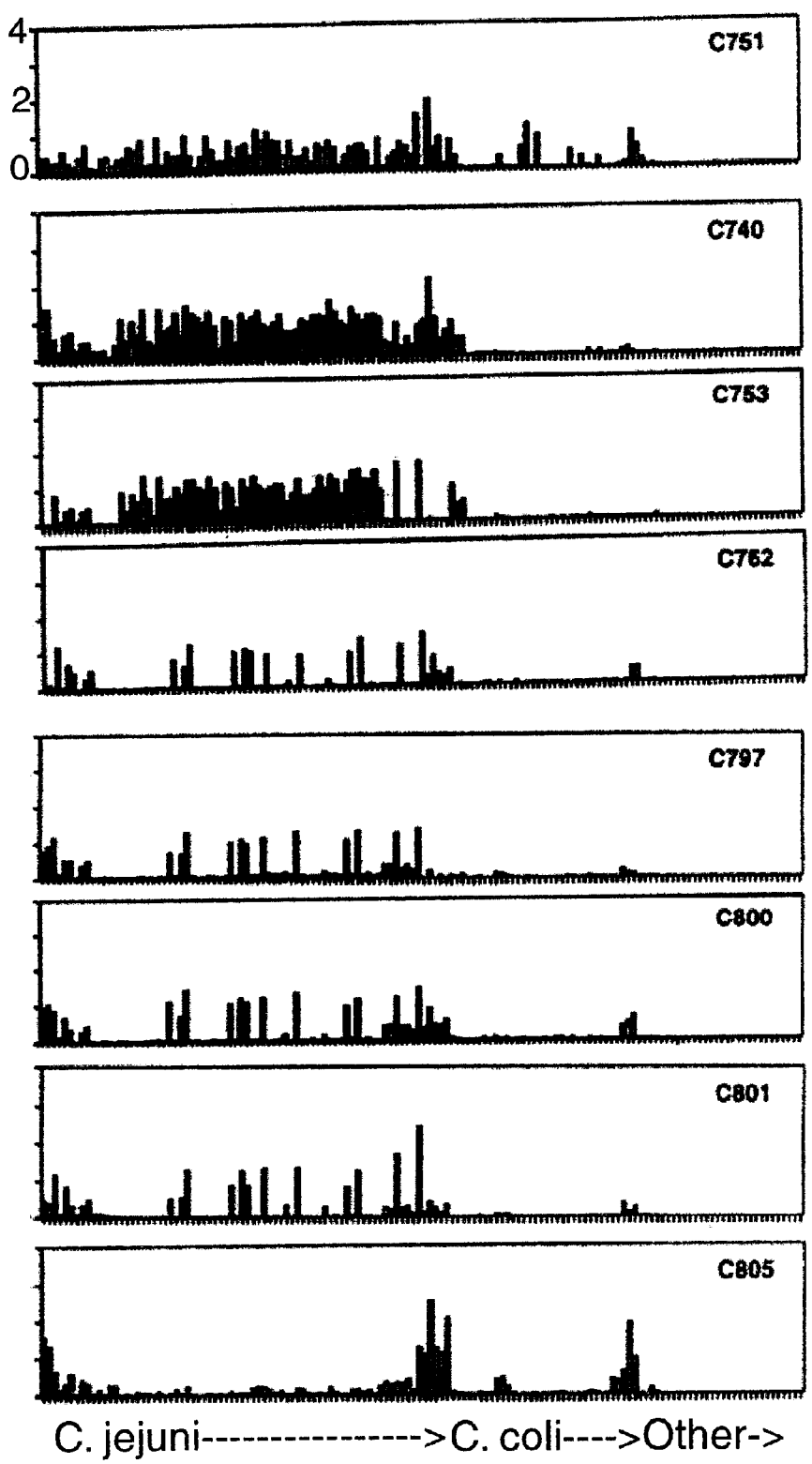
FIG. 12B shows immunoreactivity of monoclonal antibodies C751, C740, C753, C762, C797, C800, C801, and C805.

Samples of skin from a processed chicken breast purchased from a retail market were excised, incubated with a dilution of MAb C740 ascites (anti-Cj) and incubated at room temperature for 1 h. The skin was washed with water, added to a solution of fluorescein-conjugated rabbit anti-mouse IgG, incubated for 1 h, then the skin was washed again with water. The sample was fixed with a commercial tissue mounting solution and the sample was examined by laser scanning confocal microscopy (FIG. 9, magnification approximately 1000×). Single bacteria and clusters of bacteria, presumed to be Cj, were identified by the MAb. Samples incubated with the fluorescent secondary antibody alone were negative. Therefore, the epitope recognized by the anti-Cj MAb C740 appears to be expressed on naturally contaminated samples of chicken.

A recent publication provides some insight into the characteristics of the molecule(s) recognized by C731 (Bacon et al., 1999). A porin-LPS complex was purified from a clinical isolate of Cjj and shown to be cytotoxic for HEp-2, HeLa and Chinese hamster ovary cells. LPS in the complex was detected by a limulus lysate assay, and carbohydrate was detected by Schiff staining and binding of lectins specific for sialic acid, mannose, and lactosamine (Bacon et al., 1999). The *Galanthus nivalis* agglutinin bound to a carbohydrate that migrates in an SDS-PAGE gel at a very diffuse high $M_r$ region of the gel. These observations regarding the presence of a carbohydrate associated with the porin protein are consistent with our results.

REFERENCES

Acuff, G. R. (1992). Media, reagents, and stains. In Compendium of Methods for the Microbiological Examination of Foods, C. Vanderzant and D. F. Splittstoesser, eds. (Washington, D.C.: American Public Health Assoc.), pp. 1093–1208.

Anonymous (1996). Pathogen reduction: hazard analysis and critical control point (HACCP) systems. Final Rule. Federal Register 61, 38806.

Bacon, D. J., Johnson, W. M., and Rodgers, F. G. (1999). Identification and characterisation of a cytotoxic porin-lipopolysaccharide complex from *Campylobacter jejuni*. J Med Microbiol 48, 139–48.

Bolla, J. -M., Loret, E., Zalewski, M., and Pages, J. -M. (1995). Conformational analysis of the *Campylobacter jejuni* porin. J Bacteriol 177, 4266–4271.

Chaiyaroj, S. C., Sirisereewan, T., Jiamwatanasuk, N., and Sirisinha, S. (1995). Production of monoclonal antibody specific to *Campylobacter jejuni* and its potential in diagnosis of Campylobacter enteritis. Asian Pac J Allergy Immunol 13, 55–61.

Docherty, L., Adams, M. R., Patel, P., and McFadden, J. (1996). The magnetic immuno-polymerase chain reaction assay for the detection of Campylobacter in milk and poultry. Lett Appl Microbiol 22, 288–92.

Harmon, K. M., Ransom, G. M., and Wesley, I. V. (1997). Differentiation of *Campylobacter jejuni* and *Campylobacter coli* by multiplex polymerase chain reaction. Mol Cell Probes 11, 195–200.

Madden, R. H., Moran, L., and Scates, P. (1998). Frequency of occurrence of Campylobacter spp. in red meats and poultry in Northern Ireland and their subsequent subtyping using polymerase chain reaction-restriction fragment length polymorphism and the random amplified polymorphic DNA method. Journal of Applied Microbiology 84, 703–8.

Molloy, M. P., Herbert, B. R., Walsh, B. J., Tyler, M. I., Traini, M., Sanchez, J. C., Hochstrasser, D. F., Williams, K. L., and Gooley, A. A. (1998). Extraction of membrane proteins by differential solubilization for separation using two-dimensional gel electrophoresis. Electrophoresis 19, 837–44.

Nachamkin, I., Blaser, M. J., and Tompkins, L. S. (1992). *Campylobacter jejuni*: current status and future trends (Washington, D.C.: American Society for Microbiology).

Notermans, S., Zwietering, M. H., and Mead, G. C. (1994). The HACCP concept: Identification of potentially hazardous micro-organisms. Food Microbiology (London) 11, 203–214.

Oi, V. T., and Herzenberg, L. A. (1980). Selected immunoglobulin-producing hybrid cell lines. In Methods in Cellular Immunology, B. B. Mishell and S. M. Shiigi, eds. (San Francisco: W. H. Freeman), pp. 351–372.

Preston, M. A., and Penner, J. L. (1989). Characterization of cross-reacting serotypes of *Campylobacter jejuni*. Can J Microbiol 35, 265–273.

Preston, M. A., and Penner, J. L. (1987). Structural and antigenic properties of lipopolysaccharides from serotype reference strains of *Campylobacter jejuni*. Infect Immun 55, 1806–1812.

Stanley, K., Cunningham, R., and Jones, K. (1998). Isolation of *Campylobacter jejuni* from groundwater. J Appl Microbiol 85, 187–91.

Suzuki, Y., Ishihara, M., Funabashi, M., Suzuki, R., Isomura, S., and Yokochi, T. (1993). Pulsed-field gel electrophoretic analysis of *Campylobacter jejuni* DNA for use in epidemiological studies. J Infect 27, 39–42.

Uyttendaele, M., and Debevere, J. (1996). Evaluation of Preston medium for detection of *Campylobacter jejuni* in vitro and in artificially and naturally contaminated poultry products. Food Microbiol. 13, 115–122.

Vanderzant, C., and Splittstoesser, D. F. (1992). Compendium of methods for the microbiological examination of foods, 3rd Edition (Washington, D.C.: American Public Health Association).

Zhou, C., Pivarnik, P., Rand, A. G., and Letcher, S. V. (1998). Acoustic standing-wave enhancement of a fiber-optic Salmonella biosensor. Biosens Bioelectron 13, 495–500.

We claim:

1. A method of making a monoclonal antibody that is specific for epitopes shared between C. jejuni and C. coli outer membranes or that is specific for an epitope expressed on C. jejuni outer membranes, the method comprising:

(a) preparing an immunogen by isolating outer membrane complexes from each of at least two Campylobacter strains selected from the group consisting of at least one C. jejuni and at least one C. coli and pooling said isolated outer membrane complexes in approximately equivalent concentrations of the Campylobacter outer membrane complexes;

(b) immunizing animals intravenously;

(c) screening antisera of said immunized animals for antibodies that bind to C. jejuni to identify animals positive for Campylobacter antibody production;

(d) fusing isolated spleen cells from animals identified in step (c) as positive for Campylobacter antibody production and myeloma cells to obtain hybridomas;

(e) screening said hybridomas to identify hybridomas that make monoclonal antibodies that bind *Campylobacter jejuni* or bind to both C. jejuni and C. coli; and (f) screening and identifying monoclonal antibodies that:

(1) bind a conserved epitope expressed on outer membranes of C. jejuni and C. coli, wherein the monoclonal antibody binds the C. jejuni and C. coli porin protein or carbohydrate bound to porin protein, the porin comprising the 45 kD and 35 kD monomeric forms and the trimeric form of the porin; or (2) bind an epitope expressed on outer membranes of C. jejuni wherein the monoclonal antibody binds specifically to a 43–44 kD protein containing a carbohydrate moiety.

2. The method of claim 1, wherein the pooled isolated membrane complexes of the immunogen comprises an isolated membrane complex comprising at least one *Campylobacter jejuni* or C. coli strain isolated from a 1 M NaCl wash of fresh chicken epidermis.

3. The method of claim 1, wherein the immunogen of step (a) is prepared by isolating and pooling outer membrane complexes from each of at least three Campylobacter strains selected from the group consisting of at least one C. jejuni and at least one C. coli.

4. The method of claim 3, wherein the immunogen of step (a) is prepared by isolating and pooling outer membrane complexes from each of Penner lipopolysaccharide serotype reference strains O:1, O:2, O:3, O:4, O:19, O:23, O:30, O:36.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: C. jejuni and C. coli

<400> SEQUENCE: 1

Thr Pro Leu Glu Glu Ala Ile Lys Asp Val Asp Val Ser
1               5                   10

<210> SEQ ID NO 2
<211> LENGTH: 11
<212> TYPE: PRT
<213> ORGANISM: Campylobacter jejuni
<220> FEATURE:
<221> NAME/KEY: misc_feature
```

```
-continued

<222> LOCATION: ()..()
<223> OTHER INFORMATION: The undetermined amino acid may or may not
      exist

<400> SEQUENCE: 2

Xaa Thr Pro Leu Glu Glu Ala Ile Lys Asp Val
1               5                   10
```